United States Patent [19]
Krieger et al.

[11] Patent Number: 5,925,333
[45] Date of Patent: *Jul. 20, 1999

[54] METHODS FOR MODULATION OF LIPID UPTAKE

[75] Inventors: Monty Krieger, Needham; Susan L. Acton, Jamaica Plain; Attilio Rigotti, Malden, all of Mass.; Helen Haskell Hobbs; Katherine Tallman Landschulz, both of Dallas, Tex.

[73] Assignees: Massachusetts Institute of Technology, Cambridge, Mass.; Board of Regents, The University of Texas System, Austin, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/559,505

[22] Filed: Nov. 15, 1995

[51] Int. Cl.$^6$ ............................ C12N 15/09; C12N 15/79
[52] U.S. Cl. ......................... 424/9.1; 424/93.1; 435/7.2; 435/7.1; 435/7.21; 435/6
[58] Field of Search .................... 435/7.2, 961, 7.9, 435/6, 7.1, 7.21; 514/44, 2; 424/9.1, 93.1

[56] References Cited

U.S. PATENT DOCUMENTS

| | | | |
|---|---|---|---|
| 3,625,214 | 12/1971 | Higuchi | 128/260 |
| 4,244,946 | 1/1981 | River et al. | 424/177 |
| 4,305,872 | 12/1981 | Johnston et al. | 260/112.5 |
| 4,316,891 | 2/1982 | Guillemin et al. | 424/177 |
| 4,629,784 | 12/1986 | Stammer | 530/328 |
| 4,789,734 | 12/1988 | Pierschbacher . | |
| 4,792,525 | 12/1988 | Rouslaghti et al. | 435/240 |
| 4,868,116 | 9/1989 | Morgan et al. | 436/240.2 |
| 4,906,474 | 3/1990 | Langer et al. | 424/428 |
| 4,925,673 | 5/1990 | Steiner et al. | 424/458 |
| 4,980,286 | 12/1990 | Morgan et al. | 435/172.3 |
| 5,585,479 | 12/1996 | Hoke et al. | 536/24.5 |

FOREIGN PATENT DOCUMENTS

| | | |
|---|---|---|
| 3-290184 | 12/1991 | Japan . |
| 5-192179 | 11/1993 | Japan . |
| WO 90/05748 | 5/1990 | WIPO . |
| WO 93/01286 | 2/1993 | WIPO . |
| WO 93/19166 | 9/1993 | WIPO . |
| WO 96/00288 | 1/1996 | WIPO . |

OTHER PUBLICATIONS

Abrams, et al., "Macrophages in Drosophila Embryos and L2 Cells Exhibit Scavenger Receptor–mediated Endocytosis", *Proc. Natl. Acad. Sci. USA*, 89:10375–10379 (1992).

Abumrad, et al., "Cloning of a Rat Adipocyte Membrane Protein Implicated in Binding or Transport of Long–chain Fatty Acids That Is Induced during Preadipocyte Differentiation," *J. Biol. Chem.*, 268:17665–17668 (1993).

Acton, et al., "The Collagenous Domains of Macrophage Scavenger Receptors and Complement Component C1q Mediate Their Similar, But Not Identical, Binding Specificities for Polyanionic Ligands," *J. Biol. Chem.*, 268:3530–3537 (1993).

Acton, et al., "Expression Cloning of SR–BI, a CD36–related Class B Scavenger Receptor," *J. Biol. Chem.*, 269, 21003–21009 (1994).

Agrawal, et al., "Oligodeoxynucleoside phosphoramidates and phosphorothioates as inhibitors of human immunodeficiency virus," *Proc. Natl. Acad. Sci. USA*, 85:7079–7083 (1988).

*Anderson & Dietschy, *J. Biol. Chem.*, 256:7362 (1981).

Arai, et al., "Multiple Receptors for Modified Low Density Lipoproteins in Mouse Peritoneal Macrophages: Different Uptake Mechanisms for Acetylated and Oxidized Low Density Lipoproteins," *Biochem. Biophys. Res. Commun.*, 159:1375–1382 (1989).

Aruffo, & Seed, "Molecular cloning of a CD28 cDNA by a high–efficiency COS cell expression system," *Proc. Natl. Acad. Sci. USA*, 84:8573–8577 (1987).

Asch, et al., "Isolation of the Thrombospondin Membrane Receptor," *J. Clin. Invest.*, 79:1054–1061 (1987).

Ashkenas, et al., "Structures and high and low affinity ligand binding properties of murine type I and type II macrophage scavenger receptors," *J. Lipid Res.*, 34:983–1000 (1993).

Askew, et al., "Molecular Recognition with Convergent Functional Groups, Synthetic and Structural Studies with a Model Receptor for Nucleic Acid Components", *J. Am. Chem. Soc.*, 111:1082–1090 (1989).

Baldini, et al., "Cloning of a Rab3 Isotype Predominately Expressed in Adipocytes", *Proc. Natl. Acad. Sci. U.S.A.*, 89:5049–5052 (1992).

Basu, et al., "Independent Pathways for Secretion of Cholesterol and Apolipoprotein E by Macrophages", *Science*, 219:871–873 (1983).

Bickel, et al., "Rabbit Aortic Smooth Muscle Cells Express Inducible Macrophage Scavenger Receptor Messenger RNA that is Absent from Endothelial Cells", *J. Clin. Invest.*, 90:1450–1457 (1992).

Blume, et al., "Triple Helix Formation by Purine–rich Oligonucleotides Trageted to the Human Dihydrofolate Reductase Prometer", *Nucl. Acids. Res.*, 20:1777–1784 (1992).

*Bock, et al, 1992.

(List continued on next page.)

*Primary Examiner*—James Martinell
*Assistant Examiner*—Karen M. Hauda
*Attorney, Agent, or Firm*—Arnall Golden & Gregory, LLP

[57] ABSTRACT

Methods for regulation of lipid and cholesterol uptake are described which are based on regulation of the expression or function of the SR-BI HDL receptor. The examples demonstrate that estrogen dramatically downregulates SR-BI under conditions of tremendous upregulation of the LDL-receptor. The examples also demonstrate the upregulation of SR-BI in rat adrenal membranes and other non-placental steroidogenic tissues from animals treated with estrogen, but not in other non-placental non-steroidogenic tissues, including lung, liver, and skin. Examples further demonstrate the uptake of fluorescently labeled HDL into the liver cells of animal, which does not occur when the animals are treated with estrogen.

5 Claims, No Drawings

OTHER PUBLICATIONS

Brown & Goldstein, "Lipoprotein Metabolism in The Macrophage: Implications for Cholesterol Deposition in Atherosclerosis" *Annu. Rev. Biochem.*, 52:223–261 (1983).

Calvo & Vega, "Identification, Primary Structure, and Distribution of CLA–1, a Novel Member of the CD36/LIMPII Gene Family", *J. Biol. Chem.*, 268:18929:18935 (1993).

Charron, et al., "A Glucose Transport Protein Expressed Predominately in insulin–responsive Tissues", *Proc. Natl. Acad. Sci. U.S.A.*, 86:2535–2539 (1989).

Chen, et al., "NPXY, a Swquence Often Found in Cytoplasmic Tails, Is Required for Coated Pit–mediated Internalization of the Low Density Lipoprotein Receptor", *J. Biol. Chem.*, 265(6):3116–3123 (1990).

*Chung, et al. in *Methods of Enzymology*, Ed J.P. Segrest and J.J. Albers (Academic Press, Inc. Orlando, FL 1986) vol. 128, pp. 181–209.

Clackson, et al., "Making Antibory Fragments Using Phage Display Libraries", *Nature*, 352:624–628 (1991).

Cooney, et al., "Site–Specific Oligonucleotide Binding Represses Transcription of the Human c–myc Gene in Vitro", *Science*, 241:456–459 (1988).

Crooke, "Progress Toward Oligonucleotide Therapeutics: Pharmacodynamic Properties", *FASEB J.*, 7:533–539 (1993).

Cullen, Guide to Molecular Cloning Techniques: Use fo Eukaryotic Expression Technology in the Functional Analysis of Cloned Genes, *Methods in Enzymology*, 152:684–704 (1987).

Daugherty, et al., "Polymerase Chain Reaction the Cloning, CDR–grafting, and Rapid Expression of a Murine Monoclonal Antibody Directed Against the CD18 Component of Leukocyte Integrins", *Nucleic Acids Research*, 19(9):2471–2476 (1991).

De Rijke, et al., "Binding characteristics of scavenger receptors on liver endothelial and Kupffer cells for modified low–density lipoproteins," *Biochem. J.* 304:69–73 (1994).

Doi, et al., "Charged Collagen Struture Mediates the Recognition of Negatively Charged Macromolecules by Macrophage Scavenger Receptors", *J. Biol. Chem.*, 268:2126–2133 (1993).

Duval–Valentin, et al., "Specific Inhibition of Transcription by Triple Helix–Forming Oligonucleotides," *Proc. Natl. Acad. Sci. USA*, 89:504–508 (1992).

Ellington & Szostak, "Selectin in vitro of single–stranded DNA molecules that fold into specific ligand–binding structures", *Nature,* 355:850–852 (1992).

Endemann, et al. "CD36 Is a Receptor for Oxidized Low Density Lipoprotein", *J. Biol. Chem.*, 268:11811–11816 (1993).

Faust & Krieger, "Expression of Specific High Capacity Mevalonate Transport in a Chinese Hamster Ovary Cell Variant", *J. Biol. Chem.*, 262, 1996–2004 (1987).

Fraser, et al., "Divalent cation–independent macrophage adhesion inhibited by monoclonal antibody to murine scavenger receptor", *Nature*, 364:343–346 (1993).

Freeman, et al., "Expression of type I and type II bovine scavenger receptors in Chinese hamster ovary cells: Lipid droplet accumulation and nonreciprocal cross competition by acetylated and oxidized low density lipoprotein", *Proc. Natl. Acad. Sci. U.S.A.*, 88:4931–4935 (1991).

Fukasawa, et al., "Chinese Hamster Ovary Cells Expressing a Novel Type of Acetylated Low Density Lipoprotein Receptor: Isolation and Characterization", *J. Biol. Chem.*, 270(4):1921–1927 (1995).

*Glass, et al., *Proc. Natl. Acad. Sci. USA*, 80, 5435 (1983).

*Glass, et al., *J. Biol. Chem.*, 260:744 (1985).

*Goldstein, et al., in the *Metabolic and Molecular Bases of Inherited Disease*, Scriver, et al. (McGraw–Hill, NY 1995), pp. 1981–2030.

Goldstein, et al., "Binding site on macrophages that mediates uptake and degradation of acetylated low density lipoprotein, producing massive cholesterol deposition", *Proc. Natl. Acad. Sci. U.S.A.*, 76:333–337 (1979).

Goldstein, et al., "Receptor–Mediated Endocytosis of Low–Density Lipoprotein in Cultured Cells", *Methods Enzymol.*, 98:241–260 (1993).

Greenwalt, et al., "Membrane Glycoprotein CD36: A Review of Its Roles in Adherence, Signal Transduction, and Transfusion Medicine", *Blood*, 80:1105–1115 (1992).

Gregoriadis, Chapter 14: "Liposomes", *Drug Carriers in Biology and Medicine* pp. 287–341 (Academic Press, 1979).

Grigoriev, et al., "A Triple Helix–forming Oligonucleotide–Intercalator Conjugate Acts as a Transcriptional Repressor via Inhibition of NF KB Binding to Interleukin–2 receptor α–Regulatory Sequence", *J. Biol. Chem.*, 267:3389–3395 (1992).

Haberland, et al., "Two Distinct Receptors Account for Recognition of Maleyl–Albumin in Human Monocytes during differentiation In Vitro", *J. Clin. Inves.*, 77:681–689 (1986).

Haberland, et al., "Role of the Maleyl–Albumin Receptor in Activation of Murine Peritoneal Macrophages in Vitro", *J. Immunol.*, 142:855–862 (1989).

Hart & Wilcox, "A Drosophila Gene Encoding an Epithelial Membrane Protein with Homology to CD36/LIMP II", *J. Mol. Biol.*, 234:249–253 (1993).

Herz, et al., "Surface location and high affinity for calcium of a 500–kd liver membrane protein closely related to the LDL–receptor suggest a physiological role as lipoprotein receptor", *EMBO J.*, 7:4119–4127 (1988).

*Hogan, et al., Manipulating the mouse embryo, Cold Spring Harbor Laboratory, Cold Spring Harbor, NY (1986).

Holt, et al., "An Oligomer Complementary to c–myc mRNA Inhibits Proliferation of HL–60 Promyelocytic Cells and Induces Differentiation", *Mol. Cell. Biol.*, 8:963–973 (1988).

Horiuchi, et al., "Scavenger Function of Sinusoidal Liver Cells: Acetylated Low–density Lipoprotein is Endocytosed via a Route District from Formaldehyde–treated Serum Albumin", *J. Biol. Chem.*, 259:53–56 (1985).

*Huang, et al., *Proc. Natl. Acad. Sci. USA*, 88:7844–7848 (1991).

Hunt & Calderwood, "Characterization and sequence of a mouse hsp70 gene and its expression in mouse cell lines", *Gene*, 87:199–204 (1990).

Itakura, et al., "Synthesis and use of snythetic oligonucleotides", in *Ann. Rev. Biochem.*, 53:323–356 (1984).

Inaba, et al., "Macrophage Colony–stimulating Factor Regulates Both Activities of Neural and Acidic Cholesteryl Ester Hydrolases in Human Monocyte–derived Macrophages", *J. Clin. Invest.*, 92(2):750–757 (1993).

*Joyner, et al., *Nature*, 338:153–156 (1989).

*Kabat, H.A., et al., *Sequences of Proteins of Immunological Interest*, 4th Ed. (U.S. Dept. Health and Human Services, Bethesda, MD, 1987).

Kingsley, et al., "DNA–Mediated Transfer of a Human Gene Required for Low–Density Lipoprotein Receptor Expression and for Multiple Golgi Processing Pathways", *Mol. Cell. Biol.*, 6:2734–2737 (1986).

Kingsley & Krieger, "receptor–mediated endocytosis of low density lipoprotein: Somatic cell mutants define multiple genes required for expression of surface–receptor activity", *Proc Natl. Acad. Sci. USA*, 81:5454–5458 (1984).

*Khoo, et al., *J. Lipid Res.*, 36:593 (1995).

Kobzik, "Lung Macrophage Uptake of Unopsonized Environmental Particulates," *J. of Immunol.*, 155:367–376 (1995).

Kodama, et al., "Type I Macrophage Scavenger Receptor Contains Alpha–helical and Cooagen–like Coiled Coils", *Nature*, 343:531–535 (1990).

Krieger, "Complementation of Mutations in the LDL Pathway of Receptor–Mediated Endocytosis by Cocultivation of LDL Receptor–Defective Hamster Cell Mutants", *Cell*, 33: 413–422 (1983).

Krieger, "Molecular flypaper and atherosclerosis: structure of the macrophage scavenger receptor", *Trends Biochem. Sci.*, 17:141–146 (1992).

Krieger, "Reconstitution of the Hydrophobic Core of Low–Density Liproprotein", *Meth. Enzymol.*, 128:608–613 (1986).

Krieger & Herz, "Structures and Functions of Multigand Lipoprotein Receptors: Macrophage Scavenger Receptors and LDL Receptor–Related Protein (LRP)", *Annu. Rev. Biochem.*, 63:601–637 (1994).

Krieger, et al., "Amphotericin B selection of mutant Chinese hamster cells with defects in the receptor–mediated endocytosis of low density lipoprotein and cholesterol biosynthesis", *Proc. Natl. Acad. Sci. USA*, 80:5607–5611 (1983).

Krieger, et al., "Isolation of Chinese Hamster Cell Mutants Defective in the Receptor–mediated Endocytosis of Low Density Lipoprotein", *J. Mol. Biol.*, 150:167–184 (1981).

Krieger, et al., "Reconstituted Low Density Lipoprotein: A Vehicle for the Delivery of Hydrophobic Fluorescent Probes to Cells", *J. Supra. Struct.*, 10:467–478 (1979).

Krieger, et al., "Molecular Flypaper, Atherosclerosis, and Host Defense: Structure and Function of the Macrophage Scavenger Receptor", *Cold Spring Harbor Symposia On Quantitative Biology*, vol. LVII, The Cell Surface, 605–609 (1992).

Krieger, et al., "Molecular Flypaper, Host Defense, and Atherosclerosis: Structure, Binding Properties, and Functions of Macrophage Scavenger Receptors", *J. Biol. Chem.*, 268(7):4569–4572 (1993).

Lewis & Dean, "Automated site–directed drug design: the formation of molecular templates in primary structure generation", *Proc. R. Soc. Lond.*, 236:125–140 and 141–162 (1989).

Lowry, et al., "Protein Measurement with the Folin Phenol Reagent", *J. Biol. Chem.* 193:265–275 (1951).

Luoma, et al., "Expression of α2–Macroglobulin Receptor/Low Density Lipoprotein Receptor–related Protein and Scavenger Receptor in Human Atherosclerotic Lesions," *J. Clin. Invest.* 93:2014–20212 (1994).

Maher, et al., "Inhibition of DNA Binding Proteins by Oligonucleotide–Directed Triple Helix Formation",*Science*, 245:725–730 (1989).

Matsumoto, et al., "Human macrophage scavenger receptors: Primary structure, expression and localization in atherosclerotic lesions", *Proc. Natl. Acad. Sci. USA*, 87:9133–9137 (1990).

McKinlay & Rossmann, "Rational design of antiviral agents", *Annu. Rev. Pharmacol. Toxiciol.*, 29:111–122 (1989).

Merrifield, "Solid Phase Peptide Synthesis. I. The Synthesis of a Tetrapeptide", *J. Am. Chem. Soc.*, 85:2149–2154 (1963).

Moestrup, et al., "Distribution of the α2–macroglobulin receptor/low density lipoprotein receptor–related protein in human tissues", *Cell Tissue Res.*, 269:375–382 (1992).

Mulligan, "The Basic Science of Gene Therapy", *Science*, 260:926–932 (1993).

Ngelkerke, et al., "In Vivo and in Vitro Uptake and Degradation of Acetylated Low Density Lipoprotein by Rat Liver Endothelia, Kupffer, and Parenchymal Cells", *J. Biol. Chem.*, 258:12221–12227 (1983).

Naito, et al., "Tissue Distribution, Intracellular Localization, and In Vitro Expression of Bovine Macrophage Scavenber Receptors", *Am. J. Pathol.*, 139:1411–1423 (1991).

Narang, et al., in "Chemical Synthesis of Deoxyoligonucleotides by the Modified Triester Method",*Methods Enzymol.*, 65:610–620 (1980).

*Nester, et al., *Endocrinology*, 117:502 (1985).

Ockenhouse, et al., "Activation of Monocytes and Platelets by Monoclonal Antibodies or Malaria–infected Erythrocytes Binding to the CD36 Surface Receptor in vitro", *J. Clin. Invest.*, 84:468–475 (1989).

Offensperger, et al., "In vivo inhibition of duck hepatitis B virus replication and gene expression by phosphorothioate modified antisense oligodeoxynucleotides", *EMBO J.*, 12:1257–1262 (1993).

Oquendo, et al., "CD36 Directly Mediates Cytoadherence of *Plasmodium falciparium* Parasitized Erythrocites", *Cell*, 58:95–101 (1989).

Orson, et al., "Oligonucleotide inhibition of IL2Rα mRNA transcription by promoter region collinear triplex formation in lymphocytes", *Nucl. Acids Res.*, 19:3435–3441 (1991).

Ottnad, et al., "Differentiation of binding sites on reconstituted hepatic scavenger receptors using oxidized low–density lipoprotein", *Biochem J.*, 281:745–751 (1992).

Pearson, et al., "Expression cloning of dSR–CI, a class C macrophage–specific scavenger receptor from *Drosphila melanogaster*", *Proc. Natl. Acad. Sci. USA*, 92:4056–4060 (1995).

Penman, et al., "The Type I and Type II Bovine Scavenger Receptors Expressed in Chinese Hamster Ovary Cells Are Trimeric Proteins with Collagenous Triple Helical Domains Comprising Noncovalently Associated Monomers and Cys83–Disulfide–linked Dimers", *J. Biol. Chem.*, 266:23985–23993 (1991).

Perry & Davies, "The Use of 3D Modelling Databases for Identifying Structure Activity Relationship", OSAR: Quantitative Structure–Activity Relationships in Drug Design, pp. 189–193 (Alan R. Liss, Inc. 1989).

Pieters, et al., "In Vitro and In Vivo Evidence for the Role of HDL in Reverse Cholesterol Transport," *Biochim. Biophys. Acta*, 1225:125 (1994).

Pitas, et al., "Uptake of Chemically Modified Low Density Lipoproteins In Vivo Is Mediated by Specific Endothelial Cells", *J. Cell. Biol.*, 100:103–117 (1985).

*Pitas, et al., *Arterioclerosis*, 1:177 (1981).

Postel, et al., "Evidence that a triplex–forming oligodeoxyribonucleotide binds to the c–myc promoter in HeLa cells, thereby reducing c–myc mRNA levels", *Proc. Natl. Acad. Sci. USA*, 88:8227–8231 (1991).

*Potter, et al., *Proc. Natl. Acad. Sci. USA*, 81:7161 (1984).
Predescu, et al., "Binding and Transcytosis of Glycoalbumin by the Microvascular Endothelium of the Murine Myocardium: Evidence that Glycoalbumin Behaves as a Bifunctional Ligand", *J. Cell Biol.*, 107:1729–1738 (1988).
*Reaven, et al., *J. Lipid Res.*, 36:1602 (1995).
Rigotti, et al., "The Class B Scavenger Receptores SR–BI and CD36 Are Receptors for Anionic Phospholipids" *J. Bio. Chem.*, 270(27):16221–16224 (1995).
Ripka, "Computers picture the perfect drug", *New Scientist*, 54–57 (1988).
*Robertson, E. J., editor (IRL Press 1987).
Rohrer, et al., "Coiled–coil fibrous domains mediate ligand binding by macrophage scavenger receptor type II", *Nature*, 343:570–572 (1990).
Rouvinen, et al., "Computer–aided Drug Design", *Acta Pharmaceutica Fennica*, 97:159–166 (1988).
Sarin, et al., "Inhibition of acquired immunodeficiency syndrome virus by oligodeoxynucleoside methylphosphonates", *Proc. Natl. Acad. Sci. USA*, 85:7448–7451 (1989).
Savill, et al., "Macrophaage Vitronectin Receptor, CD36, and Thrombospondin Cooperate in Recognition of Neutrophils Undergoing Programmed Cell Death", *Chest*, 99:6S–7S (suppl) (1991).
Schaub, et al., "Recombinant Human Macrophage Colony-–Stimulating Factor Reduces Plasma Cholesterol and Carrageenan Granuloma Foam Cell Formation in Watanable Heritable Hyperlipidemic Rabbits", *Arterioscler. Thromb.*, 14(1):70–76 (1994).
Schnitzer, et al. "Preferential Interaction of Albumin–binding Proteins, gp30 and gp18, with Conformationally Modified Albumins", *J. Biol. Chem.*, 167:24544–24553 (1992).
*Scriver, et al., eds., in The Metabolic and Molecular Bases of Inherited Disease, vol. II, 7th Ed., pp. 2033–2034 and 2060–2061, New York: McGraw Hill.
Sege, et al., "Expression and regulation of human low–density lipoprotein receptors in Chinese hamster ovary cells", *Nature*, 307:742–745 (1984).
Sege, et al., "Characterization of a Family of Gamma–Ray-–Induced CHO Mutants Demonstrates that the IdlA Locus is Diploid and Encodes the Low–Density Lipoprotein Receptor", *Mol. Cell. Biol.*, 6:3268–3277 (1986).
Shaw, et al., "Modified deoxyoligonucleotides stable to exonuclease degradation in serum", *Nucleic Acids Res.*, 19:747–750 (1991).
Southern and Berg, *J. Mol. Appl. Gen.* 1:327–341 (1982).
Sparrow, et al., "A Macrophage Receptor That Recognizes Oxidized Low Density Lipoprotein but Not Acetylated Low Density Lipoprotein", *J. Biol. Chem.*, 264:2599–2604 (1989).
Stanton, et al. "A Macrophage Fe Receptor for IgG Is Also a Receptor for Oxidized Low Density Lipoprotein", *J. Biol. Chem.*, 267:22446–22451 (1992).

*Stein, et al., *Biochem. Biophys. Acta*, 752:98 (1983).
Steinberg, et al., "Beyond Cholesterol: Modifications of Low–Density Lipoprotein That Increase Its Atherogenicity", *N. Eng. J. Med.*, 320:915–924 (1989).
Stent & Calender, *Molecular Genetics*, W.H. Freeman & Co., pp. 213–219 (1971).
Swida, et al., "Glue Protein Genes in *Drosophila Virilis:* Their Organization, Developmental Control of Transcription and Specific mRNA Degradation", *Development*, 108:269–280 (1990).
Szostak, "In vitro genetics", *TIBS*, 17:89–93 (1992).
*Tall (Columbia University, Jammett and Tall, *J. Biol. Chem.*, 260:6687 (1985).
Tandon, et al., "Identification of Glycoprotein IV (CD36) as a Primary Receptor for Platelet–Collagen Adhesion", *J. Biol. Chem.*, 264:7576–7583 (1989).
Uhlmann & Peyman, "Antisense Oligonucleotides: A New Therapeutic Principle", Chemical Reviews, 90(4):543–584 (1990).
VandePol, et al., Clinical Applications of Recombinant Macrophage–Colony Stimulating Factor (rhM–CSF), *Biotech. Therap.*, 2:231–239 (1991).
Vega, et al., 1991, "Cloning, Sequencing, and Expression of a cDNA Encoding Rat LIMP II, a Novel 74kDa Lysosomal Membrane Protein Related to the Surface Adhesion Protein CD36", *J. Biol. Chem.*, 266:16818–16824 (1991).
Via, et al., "Identification and density dependant regulation of the AC–LDL Receptor in normal and transformed bovine aortic endothelial cells (BAEC)", *The FASEB J.*, 6:A371, #2135 (1992).
Villaschi, et al., "Binding and Uptake of Native and Glycosylated Albumin–Gold Complexes in Perfused Rat Lungs", *Microvasc. Res.*, 32:190–199 (1986).
Wickstrom, et al., "Human promyelocytic leukemia HL–60 cell proliferation and c–myc protein expression are inhibited by an antisense pentadecadeoxynucleotide targeted against c–myc mRNA", *Proc. Natl. Acad. Sci. USA*, 85:1028–1032 (1988).
Young et al., "Triple helix formation inhibits transcription elongation in vitro", *Proc. Natl. Acad. Sci. USA*, 88:10023–10026 (1991).
Zamecnik, et al., "Inhibition of Rous sarcoma virus replication and cell transformation by a specific oligodeoxynucleotide", *Proc. Natl. Acad. Sci. USA*, 75:280–284 (1978).
Zamecnik, et al., "Inhibition of replication and expression of human T–cell lymphotropic virus type III in cultured cells by exogenous systhenic oligonucleotides complementary to viral RNA", *Proc. Natl. Acad. Sci.*, 83:4143–4146 (1986).
Zhu, et al., "Systemic Gene Expression After Intravenous DNA Delivery into Adult Mice", *Science*, 261:209–211 (1993).
*Zimmer & Gruss, *Nature*, 338:150–153 (1989).

METHODS FOR MODULATION OF LIPID UPTAKE

The U.S. government has certain rights to this invention by virtue by Grants HL41484, HI-52212, and HL20948 from the National Institutes of Health-National Heart, Lung and Blood Institute.

BACKGROUND OF THE INVENTION

The present invention is generally in the area of mediation of lipid or lipoprotein uptake via the SR-B1 scavenger receptor.

The intercellular transport of lipids through the circulatory system requires the packaging of these hydrophobic molecules into water-soluble carriers, called lipoproteins, and the regulated targeting of these lipoproteins to appropriate tissues by receptor-mediated endocytic pathways. The most well characterized lipoprotein receptor is the LDL receptor, which binds to apolipoproteins B-100 (apoB-100) and E (apoE), which are constituents of low density lipoprotein, the principal cholesteryl-ester transporter in human plasma (LDL), very low-density lipoprotein, a triglyceride-rich carrier synthesized by the liver (VLDL), intermediate-density lipoprotein (IDL), and catabolized chylomicrons (dietary triglyceride-rich carriers synthesized by the liver).

All members of the LDL receptor gene family consist of the same basic structural motifs. Ligand-binding (complement-type) cysteine-rich repeats of approximately 40 amino acids are arranged in clusters (ligand-binding domains) that contain between two and eleven repeats. Ligand-binding domains are always followed by EGF-precursor homologous domains. In these domains, two EGF-like repeats are separated from a third EGF-repeat by a spacer region containing the YWTD motif. In LRP and gp330, EGF-precursor homologous domains are either followed by another ligand-binding domain or by a spacer region. The EGF-precursor homology domain, which precedes the plasma membrane, is separated from the single membrane-spanning segment either by an O-linked sugar domain (in the LDL receptor and VLDL receptor) or by one (in C. elegans and gp330) or six EGF-repeats (in LRP). The cytoplasmic tails contain between one and three "NPXY" internalization signals required for clustering of the receptors in coated pits. In a later compartment of the secretory pathway, LRP is cleaved within the eighth EGF-precursor homology domain. The two subunits LRP-515 and LRP-85 (indicated by the brackets) remain tightly and non-covalently associated. Only partial amino acid sequence of the vitellogenin receptor and of gp330 are available.

LDL receptors and most other mammalian cell-surface receptors that mediate binding and, in some cases, the endocytosis, adhesion, or signaling exhibit two common ligand-binding characteristics: high affinity and narrow specificity. However, two additional lipoprotein receptors have been identified which are characterized by high affinity and broad specificity: the macrophage scavenger receptors type I and type II.

Scavenger receptors mediate the endocytosis of chemically modified lipoproteins, such as acetylated LDL (AcLDL) and oxidized LDL (OxLDL), and have been implicated in the pathogenesis of atherosclerosis (Krieger and Herz, 1994 *J. Annu. Rev. Biochem.* 63, 601–637; Brown and Goldstein, 1983 *Annu. Rev. Biochem.* 52, 223–261; Steinberg et al., 1989 *N. Engl. J. Med.* 320, 915–924). Macrophage scavenger receptors exhibit complex binding properties, including inhibition by a wide variety of polyanions, such as maleylated BSA (M-BSA) and certain polynucleotides and polysaccharides, as well as unusual ligand-cross competition (Freeman et al., 1991 *Proc. Natl. Acad. Sci. U.S.A.* 88, 4931–4935, Krieger and Herz, 1994). Several investigators have suggested that there may be at least three different classes of such receptors expressed on mammalian macrophages, including receptors which recognize either AcLDL or OxLDL, or both of these ligands (Sparrow et al., 1989 *J. Biol. Chem.* 264, 2599–2604; Arai et al., 1989 *Biochem. Biophys. Res. Commun.* 159, 1375–1382; Nagelkerke et al., 1983 *J. Biol. Chem.* 258, 12221–12227).

The first macrophage scavenger receptors to be purified and cloned were the mammalian type I and II receptors. These are trimeric integral membrane glycoproteins whose extracellular domains have been predicted to include α-helical coiled-coil, collagenous and globular structures (Kodama et al., 1990 *Nature* 343, 531–535; Rohrer et al., 1990; Krieger and Herz, 1994). The collagenous domain, shared by the type I and type II receptors, apparently mediates the binding of polyanionic ligands (Acton et al., 1993 *J. Biol. Chem.* 268, 3530–3537; Doi et al., 1993 *J. Biol. Chem.* 268, 2126–2133). The type I and type II molecules, which are the products of alternative splicing of a single gene, are hereafter designated class A scavenger receptors (SR-AI and SR-AII). The class A receptors, which bind both AcLDL and OxLDL (Freeman et al., 1991), have been proposed to be involved in host defense and cell adhesion, as well as atherogenesis (Freeman et al., 1991; Krieger, 1992 *Trends Biochem. Sci.* 17, 141–146; Fraser et al., 1993 *Nature* 364, 343–346; Krieger and Herz, 1994).

Based on models of the predicted quaternary structures of the type I and type II macrophage scavenger receptors, both contain six domains, of which the first five are identical: the N-terminal cytoplasmic region, the transmembrane region, spacer, α-helical coil, and collagen-like domains. The C-terminal sixth domain of the type I receptor is composed of an eight-residue spacer followed by a 102-amino acid cysteine-rich domain (SRCR), while the sixth domain of the type II receptor is only a short oligopeptide.

Using a murine macrophage cDNA library and a COS cell expression cloning technique, Endemann, Stanton and colleagues, (Endemann, et al. 1993 *J. Biol. Chem.* 268, 11811–11816; Stanton, et al. *J. Biol. Chem.* 267, 22446–22451), reported the cloning of cDNAs encoding two additional proteins that can bind OxLDL. The binding of OxLDL to these proteins was not inhibited by AcLDL. These proteins are FcgRII-B2 (an Fc receptor) (Stanton et al., 1992) and CD36 (Endemann et al., 1993). The significance of the binding of OxLDL to FcgRII-B2 in transfected COS cells is unclear because FcgRII-B2 in macrophages apparently does not contribute significantly to OxLDL binding (Stanton et al., 1992). However, CD36 may play a quantitatively significant role in OxLDL binding by macrophages (Endemann et al., 1993). In addition to binding oxidized LDL, CD36 binds thrombospondin (Asch et al., 1987 *J. Clin. Invest.* 79, 1054–1061), collagen (Tandon et al., 1989 *J. Biol. Chem.* 264, 7576–7583), long-chain fatty acids (Abumrad et al., 1993 *J. Biol. Chem.* 268, 17665–17668) and *Plasmodium falciparum* infected erythrocytes (Oquendo et al., 1989 *Cell* 58, 95–101). CD36 is expressed in a variety of tissues, including adipose, and in macrophages, epithelial cells, monocytes, endothelial cells, platelets, and a wide variety of cultured lines (Abumrad et al., 1993; and see Greenwalt et al., 1992 *Blood* 80, 1105–1115 for review). Although the physiologic functions of CD36 are not known, it may serve as an adhesion molecule due to its collagen-binding properties. It is also been proposed to be a long-chain fatty acid transporter (Abumrad et al., 1993) and a signal transduction molecule (Ockenhouse et al., 1989 *J. Clin. Invest.* 84, 468–475; Huang et al., 1991), and may serve as a receptor on macrophages for senescent neutrophils (Savill et al., 1991 *Chest* 99, 7 (suppl)).

Modified lipoprotein scavenger receptor activity has also been observed in endothelial cells (Arai et al., 1989; Nagelkerke et al., 1983; Brown and Goldstein, 1983; Goldstein et al., 1979 *Proc. Natl. Acad. Sci. U.S.A.* 76, 333–337). At least some of the endothelial cell activity apparently is not mediated by the class A scavenger receptors (Bickel et al., 1992 *J. Clin. Invest.* 90, 1450–1457; Arai et al., 1989; Nagelkerke et al., 1983; Via et al., 1992 *The Faseb J.* 6, A371), which are often expressed by macrophages (Naito et al., 1991 *Am. J. Pathol.* 139, 1411–1423; Krieger and Herz, 1994). In vivo and in vitro studies suggest that there may be scavenger receptor genes expressed in endothelial cells and macrophages which differ from both the class A scavenger receptors and CD36 (Haberland et al., 1986 *J. Clin. Inves.* 77, 681–689; Via et al., 1992; Sparrow et al., 1989; Horiuchi et al., 1985 *J. Biol. Chem.* 259, 53–56; Arai et al., 1989; and see below). Via, Dressel and colleagues (Ottnad et al., 1992 *Biochem J.* 281, 745–751) and Schnitzer et al. 1992 *J. Biol. Chem.* 267, 24544–24553) have detected scavenger receptor-like binding by relatively small membrane associated proteins of 15–86 kD. In addition, the LDL receptor related protein (LRP) has been shown to bind lipoprotein remnant particles and a wide variety of other macromolecules. Both the mRNA encoding LRP and the LRP protein are found in many tissues and cell types (Herz, et al., 1988 *EMBO J.* 7:4119–4127; Moestrup, et al., 1992 *Cell Tissue Res.* 269:375–382), primarily the liver, the brain and the placenta. The predicted protein sequence of the LRP consists of a series of distinctive domains or structural motifs, which are also found in the LDL receptor.

As described by Kreiger, et al., in U.S. Ser. No. 08/265, 428 filed Jun. 23, 1994, the teachings of which are incorporated herein, two distinct scavenger receptor type proteins having high affinity for modified lipoproteins and other ligands have been isolated, characterized and cloned. Hamster and murine homolog of SR-BI, an AcLDL and LDL binding scavenger receptor, which is distinct from the type I and type II macrophage scavenger receptors, has been isolated and characterized. In addition, DNA encoding the receptor cloned from a variant of Chinese Hamster Ovary Cells, designated Var-261, has been isolated and cloned. dSR-CI, a non-mammalian AcLDL binding scavenger receptor having high ligand affinity and broad specificity, was isolated from *Drosophila melanogaster*.

It was reported by Kreiger, et al. that the SR-BI receptor is expressed principally in steroidogenic tissues and liver and appears to mediate HDL-transfer and uptake of cholesterol. Competitive binding studies show that SR-BI binds LDL, modified LDL, negatively charged phospholipid, and HDL. Direct binding studies show that SR-BI binds HDL, without degradation of the HDL-apoprotein, and lipid is accumulated within cells expressing the receptor. These studies indicate that SR-BI plays a major role in transfer of cholesterol from the liver to the steroidogenic tissues, and that increased or decreased expression in the liver or other tissues may be useful in regulating uptake of cholesterol by cells expressing SR-BI, thereby decreasing levels in foam cells and deposition at sites involved in atherogenesis.

Atherosclerosis is the leading cause of death in western industrialized countries. The risk of developing atherosclerosis is directly related to plasma levels of LDL cholesterol and inversely related to HDL cholesterol levels. Over 20 years ago, the pivotal role of the LDL receptor in LDL metabolism was elucidated by Goldstein, et al., in the Metabolic and Molecular Bases of Inherited Disease, Scriver, et al. (McGraw-Hill, N.Y. 1995), pp. 1981–2030. In contrast, the cellular mechanisms responsible for HDL metabolism are still not well defined. It is generally accepted that HDL is involved in the transport of cholesterol from extrahepatic tissues to the liver, a process known as reverse cholesterol transport, as described by Pieters, et al., *Biophys. Acta* 1225, 125 (1994), and mediates the transport of cholesteryl ester to steroidogenic tissues for hormone synthesis, as described by Andersen and Dietschy, *J. Biol. Chem.* 256, 7362 (1981). The mechanism by which HDL cholesterol is delivered to target cells differs from that of LDL. Unlike LDL, the protein components of HDL are not degraded in the process of transporting cholesterol to cells. Despite numerous attempts by many investigators, the cell-surface protein(s) that participate in the delivery of cholesterol from HDL to cells have not been identified. High density lipoprotein (HDL) and low density lipoprotein (LDL) are cholesterol transport particles whose plasma concentrations are directly (LDL) and inversely (HDL) correlated with risk for atherosclerosis. Although receptor-mediated LDL metabolism has been thoroughly described and involves cellular uptake and degradation of the entire particle, receptor-mediated HDL metabolism is not well understood. HDL, however, is known to selectively deliver its cholesterol, but not protein, to the liver and steroidogenic tissues.

It is an object of the present invention to provide to provide methods and reagents for designing drugs that can stimulate or inhibit the binding of SR-BI and redirect uptake and metabolism of lipids and cholesterol by cells.

SUMMARY OF THE INVENTION

Methods for regulation of lipid and cholesterol uptake are described which are based on regulation of the expression or function of the SR-BI HDL receptor.

The examples demonstrate that in the rat liver estrogen dramatically downregulates SR-BI under conditions of tremendous upregulation of the LDL-receptor. The examples also demonstrate the upregulation of SR-BI in rat adrenal membranes in response to estrogen, but not in other non-placental non-steroidogenic tissues, including lung, adipose tissue, and skin. Examples further demonstrate the uptake of fluorescently labeled HDL into the liver cells of rats, which does not occur when the animals are treated with estrogen.

DETAILED DESCRIPTION OF THE INVENTION

Western blotting was used to show that upon estrogen treatment in rats SR-BI levels of protein drop dramatically and LDL receptor levels increase in liver. As used herein, steroidogenic tissues refer to non-placental steroidogenic tissues including adrenal, ovary and testes. The liver and non-hepatic steroidogenic tissues have previously been shown to be sites of selective cholesterol uptake from HDL. Fluorescently labeled HDL has been used as a marker of lipid uptake and injected into estrogen and control treated animals. In control animals, there is was a significant fluorescence in liver tissue, which was totally absent in estrogen treated animals. Given that estrogen is known to cause levels of HDL to increase in humans over time and to decrease the risk of atherosclerosis and given the evidence that changes in levels of SR-BI follow estrogen administration, one could inhibit SR-BI expression in liver, thereby decreasing the risk of atherosclerosis. Inhibition can be achieved through the use of agents which inhibit expression of SR-BI, translation of SR-BI, binding of SR-BI, or cellular processing mediated by the SR-BI. Inhibition can be direct or indirect, competitive or irreversible.

I. Inhibitors of SR-BI Uptake of HDL.

Direct inhibitors include nucleotide molecules such as antisense oligonucleotides, ribozymes, and triplex forming oligonucleotides which bind to the SR-BI gene, either the protein encoding region of the gene or the regulatory regions of the gene; small organic molecules which bind to the SR-BI protein; soluble SR-BI protein or fragments thereof which competitively bind to the substrate for cell bound SR-BI; and compounds which block binding of HDL to SR-BI.

In a preferred embodiment, these compounds are initially screened using an assay such as the assays described below and then tested in transgenic animals made using standard transgenic animal technology to knockout the SR-BI gene. Since homozygous knockouts may be lethal, a technique such as embryonic stem cell technology using rats, mice or hamsters is preferred, to yield chimeric animals expressing some SR-BI.

The cDNA encoding SR-BI has been cloned. The cDNA encoding SR-BI yields a predicted protein sequence of 509 amino acids which is approximately 30% identical to those of the three previously identified CD36 family members. The cloned hamster SR-BI cDNA is approximately 2.9 kb long. The sequences of the 5' untranslated region, the coding region, and a portion of the 3' untranslated region are shown in Sequence Listing ID No. 1. The predicted protein sequence is 509 amino acids (Sequence Listing ID No. 2) with a calculated molecular weight of 57 kD. The murine cDNA is shown in Sequence Listing ID No. 3 and the predicted amino acid sequence is shown in Sequence Listing ID No. 4.

As used herein, unless specifically stated otherwise, the term "SR-BI" refers to the nucleotide and amino acid sequences, respectively, shown in Sequence ID Nos. 1 and 2, and 3 and 4, and degenerate variants thereof and their equivalents in other species of origin, especially human, as well as functionally equivalent variants, having additions, deletions, and substitutions of either nucleotides or amino acids which do not significantly alter the functional activity of the protein as a receptor characterized by the binding activity identified above.

II. Methods of Regulation of SR-BI HDL Metabolism.

It is extremely likely that SR-BI and the related SR-B proteins play critical roles in HDL mediated lipid metabolism and transport. SR-BI appears to be responsible for cholesterol delivery to steroidogenic tissues and liver. It would be useful to increase expression of SR-BI in cells in which uptake of cholesterol can be increased, freeing HDL to serve as a means for removal of cholesterol from storage cells such as foam cells where it can play a role in atherogenesis.

As discussed above, the SR-BI proteins and antibodies and their DNAs can be used in screening of drugs which modulate the activity and/or the expression of SR-BI. These drugsshould be useful in treating or preventing atherosclerosis, fat uptake by adipocytes, and some types of immune disorders.

Nucleotide Molecules

Preferred uses for the nucleotide sequences shown in the Sequence Listings below, are for the screening of drugs altering binding of or endocytosis of ligand by the scavenger receptor proteins, or expression or translation of the SR-BI protein.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text MOLECULAR GENETICS, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Screening for drugs modifying or altering the extent of receptor function or expression The receptor proteins are useful as targets for compounds which turn on, or off, or otherwise regulate binding to these receptors. The assays described below clearly provide routine methodology by which a compound can be tested for an inhibitory effect on binding of a specific compound, such as a radiolabeled modified HDL and LDL or polyion. The in vitro studies of compounds which appear to inhibit binding selectively to the receptors are then confirmed by animal testing. Since the molecules are so highly evolutionarily conserved, it is possible to conduct studies in laboratory animals such as mice to predict the effects in humans.

Studies based on inhibition of binding are predictive for indirect effects of alteration of receptor binding. For example, inhibition of LDL binding to the SR-BI receptor leads to decreased uptake by cells of LDL and therefore decreases deposition of LDL in cells; similar effects should be observed for inhibition of lipoprotein and/or lipid by cells expressing the SR-BI receptor. Conversely, increasing LDL binding to cells increases removal of lipids from the blood stream and thereby decreases lipid deposition within the blood stream. Studies have been conducted using a stimulator to enhance macrophage uptake of cholesterol and thereby treat atherogenesis, using M-CSF (Schaub, et al., 1994 *Arterioscler. Thromb.* 14.(1), 70–76; Inaba, et al., 1993 *J. Clin. Invest.* 92(2), 750–757). Although the target of the stimulator is not known with specificity, this provides further support for the rationale for believing the indirect in vivo effects can be achieved based on the in vitro binding data.

The following assays can be used to screen for compounds which are effective in methods for alter SR-BI expression, concentration, or uptake of lipid.

Assays for Alterations in SR-BI Binding or Expression

Northern blot analysis of murine tissues shows that SR-BI is most abundantly expressed in adrenal, ovary, liver, testes, and fat and is present at lower levels in some other tissues. SR-BI mRNA expression is induced upon differentiation of 3T3-L1 cells into adipocytes. Both SR-BI and CD36 display high affinity binding for acetylated LDL with an apparent dissociation constant in the range of approximately 5 $\mu$g protein/ml. The ligand binding specificities of CD36 and SR-BI, determined by competition assays, are similar, but not identical: both bind modified proteins (acetylated LDL, maleylated BSA), but not the broad array of other polyanions (e.g. fucoidin, polyinosinic acid, polyguanosinic acid) which are ligands of the class A receptors. SR-BI displays high affinity and saturable binding of HDL which is not accompanied by cellular degradation of the HDL. HDL inhibits binding of AcLDL to CD36, suggesting that it binds HDL, similarly to SR-BI. Native LDL, which does not compete for the binding of acetylated LDL to either class A receptors or CD36, competes for binding to SR-BI.

$^{125}$I-AcLDL Binding, Uptake and Degradation Assays.

Scavenger receptor activities at 37° C. are measured by ligand binding, uptake and degradation assays as described by Krieger, 1983; Freeman et al., 1991). The values for binding and uptake are combined and are presented as binding plus uptake observed after a 5 hour incubation and are expressed as ng of $^{125}$I-AcLDL protein per 5 hr per mg cell protein. Degradation activity is expressed as ng of $^{125}$I-AcLDL protein degraded in 5 hours per mg of cell protein. The specific, high affinity values represent the differences between the results obtained in the presence (single determinations) and absence (duplicate determinations) of excess unlabeled competing ligand. Cell surface 4° C. binding is assayed using either method A or method B as indicated. In method A, cells are prechilled on ice for 15 min, re-fed with $^{125}$I-AcLDL in ice-cold medium B supplemented with 10% (v/v) fetal bovine serum, with or without 75–200 μg/ml unlabeled M-BSA, and incubated 2 hr at 4° C. on a shaker. Cells are then washed rapidly three times with Tris wash buffer (50 mM Tris-HCl, 0.15 M NaCl, pH 7.4) containing 2 mg/ml BSA, followed by two 5 min washes, and two rapid washes with Tris wash buffer without BSA. The cells are solubilized in 1 ml of 0.1 N NaOH for 20 min at room temperature on a shaker, 30 μl are removed for protein determination, and the radioactivity in the remainder is determined using a LKB gamma counter. Method B differs from method A in that the cells are prechilled for 45 minutes, the medium contains 10 mM HEPES and 5% (v/v) human lipoprotein-deficient serum rather than fetal bovine serum, and the cell-associated radioactivity released by treatment with dextran sulfate is measured as described by Krieger, 1983; Freeman et al., 1991).

Northern blot analysis.

0.5 micrograms of poly(A)+ RNA prepared from different murine tissues or from 3T3-L1 cells on zero, two, four, six or eight days after initiation of differentiation into adipocytes as described by Baldini et al., 1992 *Proc. Natl. Acad. Sci. U.S.A.* 89, 5049–5052, is fractionated on a formaldehyde/agarose gel (1.0%) and then blotted and fixed onto a Biotrans™ nylon membrane. The blots are hybridized with probes that are $^{32}$P-labeled ($2\times10^6$ dpm/ml, random-primed labeling system). The hybridization and washing conditions, at 42° C. and 50° C., respectively, are performed as described by Charron et al., 1989 *Proc. Natl. Acad. Sci. U.S.A.* 86, 2535–2539. The probe for SR-BI mRNA analysis was a 0.6 kb BamHI fragment from the cDNAs coding region. The coding region of murine cytosolic hsp70 gene (Hunt and Calderwood, 1990 *Gene* 87, 199–204) is used as a control probe for equal mRNA loading.

SR-BI protein in tissues is detected by blotting with polyclonal antibodies to SR-BI.

HDL Binding Studies

HDL and VLDL binding to SR-BI and CD36 are conducted as described for LDL and modified LDL.

Studies conducted to determine if the HDL which is bound to SR-BI is degraded or recycled and if lipid which is bound to the HDL is transferred into the cells are conducted using fluorescent lipid-labeled HDL, $^3$H-cholesteryl ester labeled HDL and $^{125}$I-HDL added to cultures of transfected or untransfected cells at a single concentration (10 μg protein/ml). HDL associated with the cells is measured over time. A steady state is reached in approximately thirty minutes to one hour. A fluorescent ligand, DiI, or $^3$H-cholesterol ester is used as a marker for lipid (for example, cholesterol or cholesterol ester) uptake by the cell. Increasing concentration of DiI indicates that lipid is being transferred from the HDL to the receptor, then being internalized by the cell. The DiI-depleted HDL is then released and replaced by another HDL molecule.

HDL Binding to SR-BI

Competition binding studies demonstrate that HDL and VLDL (400 μg/ml) competitively inhibit binding of $^{125}$I-AcLDL to SR-BI. Direct binding of $^{125}$I-HDL to cells expressing SR-BI is also determined.

Tissue distribution of SR-BI

To explore the physiological functions of SR-BI, the tissue distribution of SR-BI was determined in murine tissues, both in control animals and estrogen treated animals, as described in the following examples. Each lane is loaded with 0.5 μg of poly(A)+ RNA prepared from various murine tissues: kidney, liver, adrenals, ovaries, brain, testis, fat, diaphragm, heart, lung, spleen, or other tissue. The blots are hybridized with a 750 base pair fragment of the coding region of SR-BI. SR-BI mRNA is most highly expressed in adrenals, ovary and liver is moderately or highly expressed in fat depended on the source and is expressed at lower levels in other tissues. Blots using polyclonal antibodies to a cytoplasmic region of SR-BI demonstrate that very high levels of protein are present in liver, adrenal tissues, and ovary in mice and rats, but only very low or undetectable levels are present in either white or brown fat, muscle or a variety of other tissues. Bands in the rat tissues were present at approximately 80 to 95 kD. In the mouse tissues, the 82 to 92 kD form observed in the liver and steroidogenic tissues is the same size observed in transfected cultured cells.

Assays for testing compounds for useful activity can be based solely on interaction with the receptor protein, preferably expressed on the surface of transfected cells such as those described above, although proteins in solution or immobilized on inert substrates can also be utilized, where the indication is inhibition or increase in binding of lipoproteins.

Alternatively, the assays can be based on interaction with the gene sequence encoding the receptor protein, preferably the regulatory sequences directing expression of the receptor protein. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of receptor activity in transfected or naturally occurring cells which express the receptor, then in vivo in laboratory animals. Typically, the antisense would inhibit expression. However, sequences which block those sequences which "turn off" synthesis can also be targeted.

The receptor protein for study can be isolated from either naturally occurring cells or cells which have been genetically engineered to express the receptor, as described in the examples above. In the preferred embodiment, the cells would have been engineered using the intact gene.

Random generation of receptor or receptor encoding sequence binding molecules.

Molecules with a given function, catalytic or ligand-binding, can be selected for from a complex mixture of random molecules in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process.

For example, by repeated cycles of affinity chromatography and PCR amplification of the molecules bound to the ligand on the column, Ellington and Szostak (1990) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer assisted drug design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159–166; Ripka, *New Scientist* 54–57 (Jun. 16, 1988); McKinaly and Rossmann, 1989 *Annu. Rev. Pharmacol. Toxiciol.* 29, 111–122; Perry and Davies, OSAR: Quantitative Structure-Activity Relationships in Drug Design pp. 189–193 (Alan R. Liss, Inc. 1989); Lewis and Dean, 1989 *Proc. R. Soc. Lond.* 236, 125–140 and 141–162; and, with respect to a model receptor for nucleic acid components, Askew, et al., 1989 *J. Am. Chem. Soc.* 111, 1082–1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Generation of nucleic acid regulators

Nucleic acid molecules containing the 5' regulatory sequences of the receptor genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, 1993 *Science*, 260, 926–932; U.S. Pat. No. 4,980,286; U.S. Pat. No. 4,868,116; incorporated herein by reference). Recently, a delivery system was developed in which nucleic acid is encapsulated in cationic liposomes which can be injected intravenously into a mammal. This system has been used to introduce DNA into the cells of multiple tissues of adult mice, including endothelium and bone marrow (see, e.g., Zhu et al., 1993 *Science* 261, 209–211; incorporated herein by reference).

The 5' flanking sequences of the receptor gene can also be used to inhibit the expression of the receptor. For example, an antisense RNA of all or a portion of the 5' flanking region of the receptor gene can be used to inhibit expression of the receptor in vivo. Expression vectors (e.g., retroviral expression vectors) are already available in the art which can be used to generate an antisense RNA of a selected DNA sequence which is expressed in a cell (see, e.g., U.S. Pat. No. 4,868,116; U.S. Pat. No. 4,980,286). Accordingly, DNA containing all or a portion of the sequence of the 5' flanking region of the receptor gene can be inserted into an appropriate expression vector so that upon passage into the cell, the transcription of the inserted DNA yields an antisense RNA that is complementary to the mRNA transcript of the receptor protein gene normally found in the cell. This antisense RNA transcript of the inserted DNA can then base-pair with the normal mRNA transcript found in the cell and thereby prevent the mRNA from being translated. It is of course necessary to select sequences of the 5' flanking region that are downstream from the transcriptional start sites for the receptor protein gene to ensure that the antisense RNA contains complementary sequences present on the mRNA.

Antisense RNA can be generated in vitro also, and then inserted into cells. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280–284; Zamecnik et al., 1986 *Proc. Natl. Acad. Sci.*, 83, 4143–4146; Wickstrom et al., 1988 *Proc. Natl. Acad. Sci. USA* 85, 1028–1032; Crooke, 1993 *FASEB J*. 7, 533–539. Furthermore, recent work has shown that improved inhibition of expression of a gene by antisense oligonucleotides is possible if the antisense oligonucleotides contain modified nucleotides (see, e.g., Offensperger et. al., 1993 *EMBO J*. 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079–7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448–7794 (synthesis of antisense methylphosphonate oligonucleotides); Shaw et al., 1991 Nucleic Acids Res 19, 747–750 (synthesis of 3' exonuclease-resistant oligonucleotides containing 3' terminal phosphoroamidate modifications); incorporated herein by reference).

The sequences of the 5' flanking region of receptor protein gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., *Science* 245, 725–730; Orson et al., 1991 *Nucl. Acids Res*. 19, 3435–3441; Postal et al., 1991 *Proc. Natl. Acad. Sci. USA* 88, 8227–8231; Cooney et al., 1988 *Science* 241, 456–459; Young et al., 1991 *Proc. Natl. Acad. Sci. USA* 88, 10023–10026; Duval-Valentin et al., 1992 *Proc. Natl. Acad. Sci. USA* 89, 504–508; 1992 Blume et al., *Nucl. Acids Res.* 20, 1777–1784; 1992 Grigoriev et al., *J. Biol. Chem.* 267, 3389–3395.

Recently, both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., 1988 *Mol. Cell. Biol.* 8, 963–973; Wickstrom et al., 1988 *Proc. Natl. Acad. Sci. USA* 85, 1028–1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Ikuta et al., in *Ann. Rev. Biochem.* 1984 53, 323–356 (phosphotriester and phosphite-triester methods); Narang et al., in *Methods Enzymol.*, 65, 610–620 (1980) (phosphotriester method). Accordingly, DNA sequences of the 5' flanking region of the receptor protein gene described herein can be used to design and construct oligonucleotides including a DNA sequence consisting essentially of at least 15 consecutive nucleotides, with or without base modifications or intercalating agent derivatives, for use in forming triple helices specifically within the 5' flanking region of a receptor protein gene in order to inhibit expression of the gene.

In some cases it may be advantageous to insert enhancers or multiple copies of the regulatory sequences into an expression system to facilitate screening of methods and reagents for manipulation of expression.

Preparation of Receptor Protein Fragments

Compounds which are effective for blocking binding of the receptor can also consist of fragments of the receptor proteins, expressed recombinantly and cleaved by enzymatic digest or expressed from a sequence encoding a peptide of less than the full length receptor protein. These will typically be soluble proteins, i.e., not including the transmembrane and cytoplasmic regions, although smaller portions determined in the assays described above to inhibit or compete for binding to the receptor proteins can also be utilized. It is a routine matter to make appropriate receptor protein fragments, test for binding, and then utilize. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. Based on studies with other peptide fragments blocking receptor binding, the $IC_{50}$, the dose of peptide required to inhibit binding by 50%, ranges from about 50 $\mu$M to about 300 $\mu$M, depending on the peptides. These ranges are well within the effective concentrations for the in vivo administration of peptides, based on comparison with the RGD-containing peptides, described, for example, in U.S. Pat. No. 4,792,525 to Ruoslaghti, et al., used in vivo to alter cell attachment and phagocytosis. The peptides can also be conjugated to a carrier protein such as keyhole limpet hemocyanin by its N-terminal cysteine by standard procedures such as the commercial Imject kit from Pierce Chemicals or expressed as a fusion protein, which may have increased efficacy. As noted above, the peptides can be prepared by proteolytic cleavage of the receptor proteins, or, preferably, by synthetic means. These methods are known to those skilled in the art. An example is the solid phase synthesis described by J. Merrifield, 1964 *J. Am. Chem. Soc.* 85, 2149, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305, 872 and 4,316,891. These methods can be used to synthesize peptides having identical sequence to the receptor proteins described herein, or substitutions or additions of amino acids, which can be screened for activity as described above.

The peptide can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

The peptides are generally active when administered parenterally in amounts above about 1 $\mu$g/kg of body weight. Based on extrapolation from other proteins, for treatment of most inflammatory disorders, the dosage range will be between 0.1 to 70 mg/kg of body weight. This dosage will be dependent, in part, on whether one or more peptides are administered.

Pharmaceutical Compositions

Compounds which alter receptor protein binding are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will be incorporated into an inert carrier in tablet, liquid, or capsular form. Suitable carriers may be starches or sugars and include lubricants, flavorings, binders, and other materials of the same nature. The compounds can also be administered locally by topical application of a solution, cream, gel, or polymeric material (for example, a Pluronic™, BASF).

Alternatively, the compound may be administered in liposomes or microspheres (or microparticles). Methods for preparing liposomes and microspheres for administration to a patient are known to those skilled in the art. U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979). Microspheres formed of polymers or proteins are well known to those skilled in the art, and can be tailored for passage through the gastrointestinal tract directly into the bloodstream. Alternatively, the compound can be incorporated and the microspheres, or composite of microspheres, implanted for slow release over a period of time, ranging from days to months. See, for example, U.S. Pat. Nos. 4,906,474, 4,925,673, and 3,625,214.

Generation of Transgenic Animals for Screening

With the knowledge of the cDNA encoding SR-BI and regulatory sequences regulating expression thereof, it is possible to generate transgenic animals, especially rodents, for testing the compounds which can alter SR-BI expression, translation or function in a desired manner.

There are basically two types of animals which are useful: those not expressing functional SR-BI, which are useful for testing of drugs which may work better in combination with an inhibitor of SR-BI to control levels of lipid, cholesterol, lipoprotein or components thereof, and those which overexpress SR-BI, either in those tissues which already express the protein or in those tissues where only low levels are naturally expressed.

The animals in the first group are preferably made using techniques that result in "knocking out" of the gene for SR-BI, although in the preferred case this will be incomplete, either only in certain tissues, or only to a reduced amount. These animals are preferably made using a construct that includes complementary nucleotide sequence to the SR-BI gene, but does not encode functional SR-BI, and is most preferably used with embryonic stem cells to create chimeras. Animals which are heterozygous for the defective gene can also be obtained by breeding a homozygote normal with an animal which is defective in production of SR-BI.

The animals in the second group are preferably made using a construct that includes a tissue specific promoter, of which many are available and described in the literature, or an unregulated promoter or one which is modified to increase expression as compared with the native promoter. The regulatory sequences for the SR-BI gene can be obtained using standard techniques based on screening of an appropriate library with the cDNA encoding SR-BI. These animals are most preferably made using standard microinjection techniques.

These manipulations are performed by insertion of cDNA or genomic DNA into the embryo using microinjection or other techniques known to those skilled in the art such as electroporation, as described below. The DNA is selected on the basis of the purpose for which it is intended: to inactivate the gene encoding an SR-BI or to overexpress or express in a different tissue the gene encoding SR-BI. The SR-BI encoding gene can be modified by homologous recombination with a DNA for a defective SR-BI, such as one containing within the coding sequence an antibiotic marker, which can then be used for selection purposes.

Animal Sources

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats.

Microinjection Procedures

The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art.

Transgenic Animals

Female animals are induced to superovulate using methodology adapted from the standard techniques used with mice, that is, with an injection of pregnant mare serum gonadotrophin (PMSG; Sigma) followed 48 hours later by an injection of human chorionic gonadotrophin (hCG; Sigma). Females are placed with males immediately after hCG injection. Approximately one day after hCG, the mated females are sacrificed and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult females are mated with vasectomized males to induce a false pregnancy, at the same time as donor females. At the time of embryo transfer, the recipient females are anesthetized and the oviducts are exposed by an incision through the body wall directly over the oviduct. The ovarian bursa is opened and the embryos to be transferred are inserted into the infundibulum. After the transfer, the incision is closed by suturing.

Embryonic Stem (ES) Cell Methods

Introduction of cDNA Into ES Cells:

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the SR-BI gene or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, a number of ES cells, for example, $0.5 \times 10^6$, are plated into tissue culture dishes and transfected with a mixture of the linearized nucleic acid sequence and 1 mg of pSV2neo DNA (Southern and Berg, *J. Mol. Appl. Gen.* 1:327–341 (1982)) precipitated in the presence of 50 mg lipofectin in a final volume of 100 µl. The cells are fed with selection medium containing 10% fetal bovine serum in DMEM supplemented with an antibiotic such as G418 (between 200 and 500 µg/ml). Colonies of cells resistant to G418 are isolated using cloning rings and expanded. DNA is extracted from drug resistant clones and Southern blotting experiments using the nucleic acid sequence as a probe are used to identify those clones carrying the desired nucleic acid sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989)). DNA introduction by electroporation is less efficient and requires a selection step. Methods for positive selection of the recombination event (i.e., neo resistance) and dual positive-negative selection (i.e., neo resistance and ganciclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES cell Infection

Naturally cycling or superovulated females mated with males are used to harvest embryos for the injection of ES cells. Embryos of the appropriate age are recovered after successful mating. Embryos are flushed from the uterine horns of mated females and placed in Dulbecco's modified essential medium plus 10% calf serum for injection with ES cells. Approximately 10–20 ES cells are injected into blastocysts using a glass microneedle with an internal diameter of approximately 20 µm.

Transfer of Embryos to Pseudopregnant Females

Randomly cycling adult females are paired with vasectomized males. Recipient females are mated such that they will be at 2.5 to 3.5 days post-mating (for mice, or later for larger animals) when required for implantation with blastocysts containing ES cells. At the time of embryo transfer, the recipient females are anesthetized. The ovaries are exposed by making an incision in the body wall directly over the oviduct and the ovary and uterus are externalized. A hole is made in the uterine horn with a needle through which the blastocysts are transferred. After the transfer, the ovary and uterus are pushed back into the body and the incision is closed by suturing. This procedure is repeated on the opposite side if additional transfers are to be made.

Identification of Transgenic Animals.

Samples (1–2 cm of mouse tails) are removed from young animals. For larger animals, blood or other tissue can be used. To test for chimeras in the homologous recombination experiments, i.e., to look for contribution of the targeted ES cells to the animals, coat color has been used in mice, although blood could be examined in larger animals. DNA is prepared and analyzed by both Southern blot and PCR to detect transgenic founder ($F_0$) animals and their progeny ($F_1$ and $F_2$).

Once the transgenic animals are identified, lines are established by conventional breeding and used as the donors for tissue removal and implantation using standard techniques for implantation into humans.

The present invention will be further understood by reference to the following non-limiting examples.

EXAMPLE 1

Uptake of Lipid Mediated by SR-BI

The fates of the lipid and apoprotein components of HDL after interaction with mSR-BI were compared by examining the time-course of cell association of labeled HDL, where either the proteins ($^{125}$I) or the lipids ([$^3$H]cholesteryl oleate or DiI (a fluorescent lipid)) were labeled. The kinetics of association of the protein components of HDL differed greatly from that of the lipids. Only a small fraction (<0.5%) of the total label in the $^{125}$I-HDL was bound to the transfected cells in a 5 hr period. Cell-associated $^{125}$I-HDL reached a steady-state (approximately 200 ng protein/mg cell protein at 10 µg HDL protein/ml) in less than one hour. In contrast, cell association of the lipid-labeled component of HDL ([$^3$H]cholesteryl oleate or DiI) continuously increased throughout the incubation. The kinetics of [$^3$H] cholesteryl ester and DiI transfer to the cells were similar. Approximately 18% of the total labeled lipids in HDL added to the incubation media were specifically associated with the transfected cells at the end of the 5 hr incubations. Untransfected cells displayed little lipid or protein association. Thus, there was selective transfer of the lipid, but not the protein, components of HDL to the cells expressing mSR-BI.

Uptake of Radiolabeled HDL

Methods

On day 0, ldlA cells and ldlA[mSR-BI] cells were plated in 6-well dishes (250,000 cells/well) in Ham's F-12 medium containing 100 units/ml penicillin, 100 µg/ml streptomycin, and 2 mM glutamine (medium A) supplemented with 5% fetal bovine serum (A-FBS) without or with 0.25 mg/ml G418, respectively. Assays were performed on day 2.

HDL and LDL were prepared from human plasma by zonal centrifugation (Chung, et al. in Methods of Enzymology, Ed J. P. Segrest and J. J. Albers (Academic Press, Inc. Orlando, Fla. 1986) Vol. 128, pp. 181–209. SDS-PAGE showed that the only major proteins in the HDL were apoAI and apo AII (the mass ratio of AI:AII was at least 3:1). Apo E was either undetectable or present in trace amounts. For some experiments the apo E was removed using a HiTrap Heparin column (Pharmacia) essentially as described in 'Lipoprotein Analysis: A Practical Approach'., Ed. C. A. Converse and E. R. Skinner (Oxford University Press, 1992). The mass ratio of cholesterol:protein in HDL was assumed to be 1:4. HDL was iodinated by the iodobead method (Pierce) as follows: 2 mg of HDL in 0.2 ml phosphate buffered saline ($Ca^{2+}$, $Mg^{2+}$ free) was added to 0.25 ml of 0.3 M sodium phosphate buffer, pH 7.4 containing 2 iodobeads and 1 mCi $^{125}$I-NaI. After 5 min at room temperature, the reaction was quenched with 25 µl saturated L-tyrosine (in water) and dialyzed extensively against 0.15 M NaCl, 0.3 mM EDTA, pH 7.4. The specific activities ranged from 60 to 360 cpm/ng protein. [$^3$H]cholesteryl ester labeled HDL was a gift from Alan Tall (Columbia University, Jammett and Tall, *J. Biol. Chem.* 260, 6687, (1985)).

DiI(D-282, 1,1'-dioctadecyl-3,3,3',3'-tetramethylindocarbocyanine perchlorate) was from Molecular Probes (Eugene, Oreg.). DiI-HDL was prepared essentially as described previously for DiI-LDL by Pitas, et al., *Arteriosclerosis* 1, 177 (1981)). The protein content of lipoproteins and cells was determined by the method of Lowry *J. Biol. Chem.* 193, 265 (1951)).

To determine the concentration dependence of $^{125}$I-HDL cell association (ng $^{125}$I-HDL protein associated/1.5 hr/mg cell protein), cells were refed with $^{125}$I-HDL (250 cpm/ng protein)) in medium A containing 0.5% (w/v) fatty acid free bovine serum albumin (FAF-BSA) (medium B) with or without unlabeled HDL (40-fold excess), and incubated for 1.5 hr at 37° C. in a 5% $CO_2$ humidified incubator. Cells were then chilled, rapidly washed twice with 2 ml of ice cold Tris wash buffer (50 mM Tris-HCl, 0.15 M NaCl, pH 7.4) containing 2 mg/ml BSA, once with Tris wash buffer without BSA, and radioactivity and protein determinations were made. The specific values were calculated based on the differences between the results obtained in the presence (single determinations, nonspecific activity) and absence (duplicate determinations, total activity) of excess unlabeled HDL. The time course of cell association of $^{125}$I-HDL. Cells were incubated with 20 µg protein/ml of $^{125}$I-HDL (220 cpm/ng protein) at 37° C. was determined and specific cell association (ng draft $^{125}$I-HDL protein associated/mg cell protein) was determined as described above. The time course of $^{125}$I-HDL degradation was then measured. Cells were incubated with 10 µg protein/ml of $^{125}$I-HDL (64 cpm/ng protein) and specific cellular degradation (ng of $^{125}$I-HDL protein degraded per mg of cell protein) to acid soluble products was determined.

Results

To determine if the transfer of [$^3$H]cholesteryl ester from labeled HDL represented net transfer of this lipid rather than exchange, the cholesterol contents of the cells after incubation with or without unlabeled HDL (20 µg protein/ml, 5 hrs) was compared. In the transfected cells, incubation with HDL resulted in a 20% increase (4.6 µg cholesterol/mg of cell protein) in total cellular cholesterol (free and esterified). This increase corresponded to a transfer of approximately 21% of the HDL-cholesterol added to the incubation medium and was comparable to the amounts of labeled lipid transferred from either [$^3$H]cholesteryl oleate-HDL or DiI-HDL. In contrast, there was no statistically significant HDL-dependent increase in the cholesterol content of the untransfected cells (<0.2 µg cholesterol/mg of cell protein). These results suggest that 1) mSR-BI mediated net mass transfer of HDL cholesteryl ester, 2) this transfer was quantitatively similar to that previously reported for a murine adrenal cell line (Y1-BS1), and 3) under these conditions, the fluorescent or radiolabeled lipids in HDL can serve as reasonable reporters for total cholesterol transfer.

Uptake of Fluorescent-Labeled Lipid

To begin to examine the cellular pathway of selective lipid delivery mediated by mSR-BI, the initial distribution of fluorescent lipid (DiI) delivered via the classic LDL receptor pathway with that of the mSR-BI pathway was compared.

Methods

On day 0, LDL receptor-positive wild-type CHO, mSR-BI transfected ldlA[mSR-BI], and receptor-negative ldlA cells were plated in medium A containing 5% FBS on coverslips coated with poly-D-lysine (MW>300,000, Sigma) as per the manufacturers instructions. A 600 bp probe from the hamster SR-BI cDNA described by Acton, et al., *J. Biol. Chem.* 269, 21003 (1994), the teachings of which are incorporated herein, was used to screen a murine 3T3-L1 adipocyte cDNA library. A clone containing the complete coding region was isolated and this region was sequenced on both strands; the sequence had 89% predicted amino acid identity and 96% similarity to the hamster sequence and 79% predicted amino acid identity and 91% similarity to the human sequence, CLA1 (Calvo and Vega, *J. Biol. Chem.* 268, 18929 (1993), the teachings of which are incorporated herein. The expression vector pmSR-BI-77 was generated from this clone and, using previously described methods, transfected into an LDL receptor-negative mutant CHO cell line, 1d1A, to generate stable, receptor-positive transfectants. Flow cytometry after incubation with DiI-labeled acetylated LDL was used to isolate the subpopulation of cells, 1d1A[mSR-BI] (colony 15), used here.

On day 1, the monolayers were refed with medium A containing 5% newborn calf lipoprotein-deficient serum. On day 3 the subconfluent cells were refed with the same medium containing either 10 µg protein/ml DiI-LDL (A) or 1 µg protein/ml of DiI-HDL (B and C) and incubated for 1 hr at 37° C. The coverslips were then washed once with phosphate buffered saline and the distribution of DiI was immediately recorded photographically using a Nikon fluorescence microscope with a rhodamine filter package.

Cells were plated and on day 2 were incubated at 37° C. in medium B containing either $^{125}$I-HDL (10 µg protein/ml, 64 cpm/ng protein), $^3$H-cholesteryl oleate-labeled HDL (2.2 µg cholesteryl ester/ml; 15 cpm/ng cholesteryl ester; approximately 8.8 µg protein/ml) or DiI-labeled HDL (10 µg protein/ml). The cells were then washed and cell-associated label was determined as follows: $^{125}$I-HDL was determined as described above. $^3$H-cholesteryl oleate was extracted with isopropyl alcohol for 30 min at room temperature, and radioactivity was measured in Scintiverse II (Fisher) scintillation mixture. DiI was extracted by dissolving the cells in DMSO and measuring the fluorescence in a Hitachi model F-4500 fluorescence spectrophotometer at 550 nm excitation, 565 nm emission and compared to standards prepared of DiI-HDL dissolved in DMSO. Cells were plated as described above except medium A contained 3% newborn calf lipoprotein-deficient serum in place of FBS. On day 2, cells were incubated for 5 h at 37° C. in medium B in the presence or absence of unlabeled HDL (20 µg protein/ml), washed as described above, and lipids were extracted twice with hexane/isopropanol (3:2, 3 ml, 30 min). Extracts were pooled, backextracted with 1 ml water, and dried by rotary evaporation. Total (free and esterified) cholesterol masses (averages of six replicates) were determined using an enzymatic assay (Sigma Diagnostics, St. Louis, Mo.). The protein contents of the samples were estimated by analysis of replicate cultures. The values of total cholesterol (µg,/mg cell protein ± SEM for the cells incubated without HDL were 20.5±0.3 (1d1A) and 23.0±0.4 (1d1A[mSR-BI]). The specific values represent the differences between values obtained in the absence (total, duplicate incubations) and presence (nonspecific, single incubations) of an excess of unlabeled HDL (400 µg protein/ml) and are expressed as the percent of total label added to the wells.

Results

After LDL receptor-positive wild-type CHO cells were incubated with DiI-LDL (10 µg protein/ml) for one hr at 37° C., uptake via the classic LDL receptor resulted in a punctate pattern of labeling. This was typical for receptor-mediated endocytosis from coated pits and vesicles to endosomes and lysosomes. There was essentially no labeling by DiI-LDL of LDL receptor-negative ldlA cells. DiI-HDL (1 µg protein/ml) labeling of ldlA[mSR-BI] cells was dramatically different—rather than punctate fluorescence, there was diffuse staining over what appeared to be the entire surface of the transfected cells, with especially striking fluorescence at cell-cell interfaces. In addition, there was often a bright, apparently internal, concentration of fluorescence in a region adjacent to the nucleus. Even after 24 hrs of incubation, the DiI-fluorescence pattern in the mSR-BI transfectants did not resemble the punctate pattern seen for the LDL receptor pathway, although the pattern differed and possibly represents the subsequent redistribution of the dye away from the plasma membrane. Untransfected ldlA cells did not accumulate significant levels of dye from DiI-HDL. It is important to note that the initial distribution (less than or equal one hr) as well as the subsequent sites of accumulation of DiI, a positively charged lipid, may differ from those of cholesteryl ester, a neutral lipid. Indeed, it was observed that, after 48 hr of incubation with unlabeled HDL, neutral lipids transferred to the transfected cells apparently accumulated in small, well-defined cytoplasmic particles which stained with oil red O. Similarly, Reaven, et al., *J. Lipid Res.* 36, 1602 (1995), have reported the accumulation of a fluorescent cholesteryl ester derivative into cytoplasmic fat droplets in ovarian granuloma cells after a 9 hr incubation of the cells with labeled HDL. Taken together, these results indicate that the pathway by which mSR-BI mediates lipid transfer from HDL is distinct from the classic LDL receptor-mediated endocytic pathway and suggest that the HDL lipids may initially be transferred directly from the lipoprotein to the plasma membrane.

EXAMPLE 2

Tissue Distribution of SR-BI

In vivo metabolic studies have established that the liver and steroidogenic tissues (adrenal and ovary) are the primary tissues involved in the selective uptake of HDL-cholesteryl esters, Glass, et al., *Proc. Natl. Acad. Sci. USA* 80, 5435 (1983), *J. Biol. Chem.* 260, 744 (1985), Khoo, et al., *J. Lipid Res.* 36, 593 (1995), Stein, et al., *Biochim. Biophys. Acta* 752, 98 (1983), Nestler, et al., *Endocrinology* 117, 502 (1985). Although numerous ligand blotting studies of these tissues have revealed a variety of HDL binding proteins ranging in size from 58 kD to 140 kD, none of these has directly been shown to mediate selective lipid uptake.

Methods

To determine the size of mSR-BI and its tissue distribution, a rabbit anti-mSR-BI polyclonal antibody was prepared by immunization of a 16 amino acid peptide (residues 495 to 509 from the predicted protein sequence of mSR-BI plus an additional N-terminal cysteine) coupled to keyhole limpet hemocyanin. This is referred to as anti-mSR-BI$^{495}$ antiserum. The antiserum was used for immunoblot analysis of cultured cells and murine tissues.

Post-nuclear cell extracts from ldlA and ldlA[mSR-BI] cells and membranes (post-nuclear 100,000×g pellets) from murine tissues were isolated, reduced, and separated by 6.5% SDS-polyacrylamide gel electrophoresis (50 μg protein/lane), transferred to nitrocellulose and probed with a primary anti-mSR-BI$^{495}$ antipeptide antibody (rabbit IgG fraction, 1:5000 dilution) and developed using a horseradish peroxidase labeled second antibody and ECL kit (5 min exposure, Amersham). Ponceau S staining was used as a control for gel loading and transfer.

Results

The antibody recognized an approximately 82 kD protein in transfected cells (ldlA[mSR-BI]) which was not present in the untransfected cells (ldlA). The predicted mass of the mSR-BI polypeptide is 57 kD, suggesting mSR-BI underwent significant co- and/or post-translational modification.

mSR-BI was most highly expressed in three tissues, liver and the steroidogenic ovary and adrenal glands. Significantly less mSR-BI protein was detected in testis, heart and mammary gland and essentially no expression was observed in other tissues, including brain, kidney, spleen, muscle, uterus, intestine, epididymal fat, lung and placenta. Thus, SR-BI is most abundantly expressed in precisely those tissues exhibiting selective cholesteryl ester transport in vivo.

A substantial signal in murine fat tissue and cultured adipocytes had been observed in previous Northern blotting studies using a hamster SR-BI cDNA probe. This lack of correlation with the immunoblot results reported here may be due to tissue specific differences in translational regulation or protein stability, or to cross hybridization of the hamster cDNA probe with mRNA of a related, but distinct, gene which is highly expressed in fat.

EXAMPLE 3

Analysis of Estrogen-Treated Rat Tissues for Expression of SR-BI

Methods

Tissues of estrogen-treated rats were screened for expression of SR-BI as described above following treatment of rats with 17-α-ethylenyl estradiol (estrogen). The rats were treated for five consecutive days with subcutaneous injections of 5 mg/kg 17-α-ethylenyl estradiol in propylene glycol or with propylene glycol alone (sham-injected).

Results

Immunoblots comparing the expression of SR-BI in rat tissues in estrogen-treated or sham-treated animals show the upregulation of SR-BI in rat adrenal membranes from animals treated with estrogen as compared with controls. There is no change in SR-BI levels in tissues showing trace signal, including lung as well as testes and skin. A longer exposure, comparing a SR-BI positive control and negative control, with liver tissues from estrogen treated and sham treated animals, and adrenal tissues from estrogen treated and sham treated animals show the same results.

Immunoblots comparing expression of the SR-BI and LDL receptor show that SR-BI expression was dramatically downregulated under conditions of tremendous upregulation of the LDL-receptor.

EXAMPLE 4

Analysis of Lipid Uptake in Estrogen Treated Animals

When HDL labeled fluorescently with DI, as described above, was injected into the treated and control animals, sham injected rats with apparent HDL-receptors had visible uptake of HDL-derived lipids into their liver cells, whereas estrogen-treated animals had no similar uptake in the liver cells. The uptake of lipid into adrenal tissues was also dramatically increased in the estrogen-treated animals.

Modifications and variations of the methods and materials described herein will be obvious to those skilled in the art and are intended to be encompassed by the following claims. The teachings of the references cited herein are specifically incorporated herein.

We claim:

1. An in vitro method of screening for a compound which alters the binding or uptake of cholesteryl esters or other lipids bound to or complexed with high density lipoprotein by a mammalian scavenger receptor protein type BI comprising:

provding an assay for measuring binding or uptake by the scavenger receptor protein of cholesteryl esters or other lipids bound to or complexed with high density lipoprotein;

adding the compound to be tested to the assay; and determining if the amount of cholesteryl ester or other lipids bound to or complexed with high density lipoprotein which is bound to or taken up by the scavenger receptor protein is altered as compared to binding or uptake in the absence of the compound to be tested, wherein a difference in binding or uptake by a mammalian scavenger receptor protein type BI identifies a compound which alters the binding or uptake of cholesteryl esters or other lipids bound to or complexed with high density lipoprotein.

2. The method of claim 1 wherein the assay includes a cell expressing the scavenger receptor protein and the compound is a nucleic acid sequence which potentially alters expression of the scavenger receptor protein.

3. The method of claim 1 wherein the compound is selected from a library of naturally occurring or synthetic compounds which are randomly tested for alteration of binding.

4. The method of claim 1 wherein the compound competitively inhibits binding to the scavenger receptor protein.

5. A method of screening for a compound which alters the activity of mammalian scavenger receptor protein type BI (SR-BI) comprising:

administering the compound to a mammal naturally expressing the SR-BI;

measuring expression of SR-BI mRNA or protein in tissues of the mammal or measuring SR-BI-mediated binding or transport of cholesteryl esters or other lipids bound to or complexed with high density lipoprotein, and measuring at least one parameter selected from the group consisting of lipid levels, lipoprotein levels, cholesterol levels, production of steroid hormones, bile acid levels, vitamin D levels, and alterations of the chemical composition of lipids, lipoproteins, cholesterol, steroid hormones, bile acids, and vitamin D; and comparing the measured expression levels or binding and transport of cholesteryl esters or other lipids, and other measured parameters after the administration of the compound with the measured expression levels or binding and transport of cholesteryl esters or other lipids, and other measured parameters prior to administration of the compound, wherein differences in the measurements taken before and after administration of the compound identifies a compound which alters the activity of the SR-BI.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1788 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: misc_feature
      (B) LOCATION: 156..1683
      (D) OTHER INFORMATION: /function= "Nucleotides 156 through
          1683 encode the amino acid sequence for the Hamster
          Scavenger Receptor Class B-I."

(xi) SEQUENCE DESCRIPTION: SEQ ID NO:1:

```
GCCACCTGCA GGGCTACTGC TGCTCCGGCC ACTGCCTGAG ACTCACCTTG CTGGAACGTG      60

AGCCTCGGCT TCTGTCATCT CTGTGGCCTC TGTCGCTTCT GTCGCTGTCC CCCTTCAGTC     120

CCTGAGCCCC GCGAGCCCGG GCCGCACACG CGGAC ATG GGC GGC AGC GCC AGG        173
                                       Met Gly Gly Ser Ala Arg
                                         1               5

GCG CGC TGG GTG GCG GTG GGG CTG GGC GTC GTG GGG CTG CTG TGC GCT      221
Ala Arg Trp Val Ala Val Gly Leu Gly Val Val Gly Leu Leu Cys Ala
             10                  15                  20

GTG CTC GGT GTG GTT ATG ATC CTC GTG ATG CCC TCG CTC ATC AAA CAG      269
Val Leu Gly Val Val Met Ile Leu Val Met Pro Ser Leu Ile Lys Gln
         25                  30                  35

CAG GTA CTG AAG AAT GTC CGC ATA GAC CCC AGC AGC CTG TCC TTT GCA      317
Gln Val Leu Lys Asn Val Arg Ile Asp Pro Ser Ser Leu Ser Phe Ala
     40                  45                  50

ATG TGG AAG GAG ATC CCT GTA CCC TTC TAC TTG TCC GTC TAC TTC TTC      365
Met Trp Lys Glu Ile Pro Val Pro Phe Tyr Leu Ser Val Tyr Phe Phe
 55                  60                  65                  70

GAG GTG GTC AAT CCC AGC GAG ATC CTA AAG GGT GAG AAG CCA GTA GTG      413
Glu Val Val Asn Pro Ser Glu Ile Leu Lys Gly Glu Lys Pro Val Val
                 75                  80                  85

CGG GAG CGT GGA CCC TAT GTC TAC AGG GAA TTC AGA CAT AAG GCC AAC      461
Arg Glu Arg Gly Pro Tyr Val Tyr Arg Glu Phe Arg His Lys Ala Asn
             90                  95                 100

ATC ACC TTC AAT GAC AAT GAT ACT GTG TCC TTT GTG GAG CAC CGC AGC      509
Ile Thr Phe Asn Asp Asn Asp Thr Val Ser Phe Val Glu His Arg Ser
        105                 110                 115

CTC CAT TTC CAG CCG GAC AGG TCC CAC GGC TCT GAG AGT GAC TAC ATT      557
Leu His Phe Gln Pro Asp Arg Ser His Gly Ser Glu Ser Asp Tyr Ile
    120                 125                 130

ATA CTG CCT AAC ATT CTG GTC TTG GGG GCA GTA ATG ATG GAG AGC          605
Ile Leu Pro Asn Ile Leu Val Leu Gly Ala Val Met Met Glu Ser
135                 140                 145                 150

AAG TCT GCA GGC CTG AAG CTG ATG ATG ACC TTG GGC CTG GCC ACC TTG      653
Lys Ser Ala Gly Leu Lys Leu Met Met Thr Leu Gly Leu Ala Thr Leu
                155                 160                 165

GGC CAG CGT GCC TTT ATG AAC CGA ACA GTT GGT GAG ATC CTG TGG GGC      701
```

-continued

```
Gly Gln Arg Ala Phe Met Asn Arg Thr Val Gly Glu Ile Leu Trp Gly
            170                 175                 180

TAT GAG GAT CCC TTC GTG AAT TTT ATC AAC AAA TAC TTA CCA GAC ATG      749
Tyr Glu Asp Pro Phe Val Asn Phe Ile Asn Lys Tyr Leu Pro Asp Met
            185                 190                 195

TTC CCC ATC AAG GGC AAG TTC GGC CTG TTT GTT GAG ATG AAC AAC TCA      797
Phe Pro Ile Lys Gly Lys Phe Gly Leu Phe Val Glu Met Asn Asn Ser
200                 205                 210

GAC TCT GGG CTC TTC ACT GTG TTC ACG GGC GTC CAG AAC TTC AGC AAG      845
Asp Ser Gly Leu Phe Thr Val Phe Thr Gly Val Gln Asn Phe Ser Lys
215                 220                 225                 230

ATC CAC CTG GTG GAC AGA TGG AAT GGG CTC AGC AAG GTC AAC TAC TGG      893
Ile His Leu Val Asp Arg Trp Asn Gly Leu Ser Lys Val Asn Tyr Trp
                235                 240                 245

CAT TCA GAG CAG TGC AAC ATG ATC AAT GGC ACT TCC GGG CAG ATG TGG      941
His Ser Glu Gln Cys Asn Met Ile Asn Gly Thr Ser Gly Gln Met Trp
            250                 255                 260

GCA CCA TTC ATG ACA CCC CAG TCC TCG CTG GAA TTC TTC AGT CCG GAA      989
Ala Pro Phe Met Thr Pro Gln Ser Ser Leu Glu Phe Phe Ser Pro Glu
            265                 270                 275

GCC TGC AGG TCT ATG AAG CTC ACC TAC CAT GAT TCA GGG GTG TTT GAA     1037
Ala Cys Arg Ser Met Lys Leu Thr Tyr His Asp Ser Gly Val Phe Glu
280                 285                 290

GGC ATC CCC ACC TAT CGC TTC ACA GCC CCT AAA ACT TTG TTT GCC AAT     1085
Gly Ile Pro Thr Tyr Arg Phe Thr Ala Pro Lys Thr Leu Phe Ala Asn
295                 300                 305                 310

GGG TCT GTT TAC CCA CCC AAT GAA GGT TTC TGC CCG TGC CTT GAA TCC     1133
Gly Ser Val Tyr Pro Pro Asn Glu Gly Phe Cys Pro Cys Leu Glu Ser
                315                 320                 325

GGC ATT CAA AAT GTC AGC ACT TGC AGG TTT GGT GCA CCC CTG TTT CTG     1181
Gly Ile Gln Asn Val Ser Thr Cys Arg Phe Gly Ala Pro Leu Phe Leu
            330                 335                 340

TCA CAC CCT CAC TTC TAC AAT GCA GAC CCT GTG CTA TCA GAA GCC GTT     1229
Ser His Pro His Phe Tyr Asn Ala Asp Pro Val Leu Ser Glu Ala Val
            345                 350                 355

CTG GGT CTG AAC CCT GAC CCA AGG GAG CAT TCT TTG TTC CTT GAC ATC     1277
Leu Gly Leu Asn Pro Asp Pro Arg Glu His Ser Leu Phe Leu Asp Ile
360                 365                 370

CAT CCG GTC ACT GGG ATC CCC ATG AAC TGT TCT GTG AAG TTG CAG ATA     1325
His Pro Val Thr Gly Ile Pro Met Asn Cys Ser Val Lys Leu Gln Ile
375                 380                 385                 390

AGC CTC TAC ATC AAA GCT GTC AAG GGC ATT GGG CAA ACA GGG AAG ATC     1373
Ser Leu Tyr Ile Lys Ala Val Lys Gly Ile Gly Gln Thr Gly Lys Ile
                395                 400                 405

GAG CCC GTG GTC CTC CCA TTG CTG TGG TTT GAG CAG AGC GGT GCC ATG     1421
Glu Pro Val Val Leu Pro Leu Leu Trp Phe Glu Gln Ser Gly Ala Met
            410                 415                 420

GGC GGC GAG CCC CTG AAC ACG TTC TAC ACG CAG CTG GTG CTG ATG CCC     1469
Gly Gly Glu Pro Leu Asn Thr Phe Tyr Thr Gln Leu Val Leu Met Pro
            425                 430                 435

CAG GTA CTT CAG TAT GTG CAG TAT GTG CTG CTG GGG CTG GGC GGC CTC     1517
Gln Val Leu Gln Tyr Val Gln Tyr Val Leu Leu Gly Leu Gly Gly Leu
            440                 445                 450

CTG CTG CTG GTG CCC GTC ATC TAC CAG TTG CGC AGC CAG GAG AAA TGC     1565
Leu Leu Leu Val Pro Val Ile Tyr Gln Leu Arg Ser Gln Glu Lys Cys
455                 460                 465                 470

TTT TTA TTT TGG AGT GGT AGT AAA AAG GGC TCG CAG GAT AAG GAG GCC     1613
Phe Leu Phe Trp Ser Gly Ser Lys Lys Gly Ser Gln Asp Lys Glu Ala
                475                 480                 485

ATT CAG GCC TAC TCT GAG TCT CTG ATG TCA CCA GCT GCC AAG GGC ACG     1661
Ile Gln Ala Tyr Ser Glu Ser Leu Met Ser Pro Ala Ala Lys Gly Thr
```

```
Ile Gln Ala Tyr Ser Glu Ser Leu Met Ser Pro Ala Ala Lys Gly Thr
            490                 495                 500

GTG CTG CAA GAA GCC AAG CTG T AGGGTCCCAA AGACACCACG AGCCCCCCCA        1713
Val Leu Gln Glu Ala Lys Leu
            505

ACCTGATAGC TTGGTCAGAC CAGCCATCCA GCCCCTACAC CCCGCTTCTT GAGGACTCTC    1773

TCAGCGGACA GTCGC                                                     1788

(2) INFORMATION FOR SEQ ID NO:2:

(i) SEQUENCE CHARACTERISTICS:
        (A) LENGTH: 509 amino acids
        (B) TYPE: amino acid
        (D) TOPOLOGY: linear (ii) MOLECULE TYPE: protein (iii) HYPOTHETICAL: NO (v) FRAGMENT TYPE: internal (ix) FEATURE:
        (A) NAME/KEY: misc_feature
        (B) LOCATION: 1..509
        (D) OTHER INFORMATION: /function= "Amino acid sequence for
            the Hamster Scavenger Receptor Class B-I."

(ix) FEATURE:
        (A) NAME/KEY: Domain
        (B) LOCATION: 9..32
        (D) OTHER INFORMATION: /note= "Putative transmembrane
            domain."

(ix) FEATURE:
        (A) NAME/KEY: Domain
        (B) LOCATION: 440..464
        (D) OTHER INFORMATION: /note= "Putative transmembrane
            domain."

(ix) FEATURE:
        (A) NAME/KEY: Modified-site
        (B) LOCATION: 1..385
        (D) OTHER INFORMATION: /note= "Positions 102-104, 108-110,
            173-175, 212-214, 227-229, 255-257, 310-312, 330-332
            and 383-385 represent potential N-linked glycosylation
            sites."

(ix) FEATURE:
        (A) NAME/KEY: Modified-site
        (B) LOCATION: 21..470
        (D) OTHER INFORMATION: /note= "The cysteines at positions
            21, 251, 280, 321, 323, 334, 384 and 470 represent
            potential disulfide linkages."

(xi) SEQUENCE DESCRIPTION: SEQ ID NO:2:

Met Gly Gly Ser Ala Arg Ala Arg Trp Val Ala Val Gly Leu Gly Val
1               5                   10                  15

Val Gly Leu Leu Cys Ala Val Leu Gly Val Val Met Ile Leu Val Met
            20                  25                  30

Pro Ser Leu Ile Lys Gln Gln Val Leu Lys Asn Val Arg Ile Asp Pro
        35                  40                  45

Ser Ser Leu Ser Phe Ala Met Trp Lys Glu Ile Pro Val Pro Phe Tyr
    50                  55                  60

Leu Ser Val Tyr Phe Phe Glu Val Val Asn Pro Ser Glu Ile Leu Lys
65                  70                  75                  80

Gly Glu Lys Pro Val Val Arg Glu Arg Gly Pro Tyr Val Tyr Arg Glu
                85                  90                  95

Phe Arg His Lys Ala Asn Ile Thr Phe Asn Asp Asn Asp Thr Val Ser
            100                 105                 110
```

-continued

```
Phe Val Glu His Arg Ser Leu His Phe Gln Pro Asp Arg Ser His Gly
            115                 120                 125

Ser Glu Ser Asp Tyr Ile Ile Leu Pro Asn Ile Leu Val Leu Gly Gly
            130                 135                 140

Ala Val Met Met Glu Ser Lys Ser Ala Gly Leu Lys Leu Met Met Thr
145                 150                 155                 160

Leu Gly Leu Ala Thr Leu Gly Gln Arg Ala Phe Met Asn Arg Thr Val
                165                 170                 175

Gly Glu Ile Leu Trp Gly Tyr Glu Asp Pro Phe Val Asn Phe Ile Asn
                180                 185                 190

Lys Tyr Leu Pro Asp Met Phe Pro Ile Lys Gly Lys Phe Gly Leu Phe
                195                 200                 205

Val Glu Met Asn Asn Ser Asp Ser Gly Leu Phe Thr Val Phe Thr Gly
            210                 215                 220

Val Gln Asn Phe Ser Lys Ile His Leu Val Asp Arg Trp Asn Gly Leu
225                 230                 235                 240

Ser Lys Val Asn Tyr Trp His Ser Glu Gln Cys Asn Met Ile Asn Gly
                245                 250                 255

Thr Ser Gly Gln Met Trp Ala Pro Phe Met Thr Pro Gln Ser Ser Leu
                260                 265                 270

Glu Phe Phe Ser Pro Glu Ala Cys Arg Ser Met Lys Leu Thr Tyr His
            275                 280                 285

Asp Ser Gly Val Phe Glu Gly Ile Pro Thr Tyr Arg Phe Thr Ala Pro
            290                 295                 300

Lys Thr Leu Phe Ala Asn Gly Ser Val Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Gly Ala Pro Leu Phe Leu Ser His Pro His Phe Tyr Asn Ala Asp Pro
                340                 345                 350

Val Leu Ser Glu Ala Val Leu Gly Leu Asn Pro Asp Pro Arg Glu His
            355                 360                 365

Ser Leu Phe Leu Asp Ile His Pro Val Thr Gly Ile Pro Met Asn Cys
            370                 375                 380

Ser Val Lys Leu Gln Ile Ser Leu Tyr Ile Lys Ala Val Lys Gly Ile
385                 390                 395                 400

Gly Gln Thr Gly Lys Ile Glu Pro Val Val Leu Pro Leu Leu Trp Phe
                405                 410                 415

Glu Gln Ser Gly Ala Met Gly Gly Glu Pro Leu Asn Thr Phe Tyr Thr
                420                 425                 430

Gln Leu Val Leu Met Pro Gln Val Leu Gln Tyr Val Gln Tyr Val Leu
            435                 440                 445

Leu Gly Leu Gly Gly Leu Leu Leu Val Pro Val Ile Tyr Gln Leu
            450                 455                 460

Arg Ser Gln Glu Lys Cys Phe Leu Phe Trp Ser Gly Ser Lys Gly
465                 470                 475                 480

Ser Gln Asp Lys Glu Ala Ile Gln Ala Tyr Ser Glu Ser Leu Met Ser
                485                 490                 495

Pro Ala Ala Lys Gly Thr Val Leu Gln Glu Ala Lys Leu
                500                 505
```

(2) INFORMATION FOR SEQ ID NO:3:

(i) SEQUENCE CHARACTERISTICS:

(A) LENGTH: 1785 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (ix) FEATURE:
(A) NAME/KEY: CDS
(B) LOCATION: 51..1577
(D) OTHER INFORMATION: /Function = "Nucleotides 51 through 1577 encode the amino acid sequence for the murine Scavenger Receptor Class BI."

(xi) SEQUENCE DESCRIPTION: SEQ ID NO:3:

```
CCGTCTCCTT CAGGTCCTGA GCCCCGAGAG CCCCTTCCGC GCACGCGGAC ATG GGC         56
                                                      Met Gly
                                                        1

GGC AGC TCC AGG GCG CGC TGG GTG GCC TTG GGG TTG GGC GCC CTG GGG       104
Gly Ser Ser Arg Ala Arg Trp Val Ala Leu Gly Leu Gly Ala Leu Gly
         5                  10                  15

CTG CTG TTT GCT GCG CTC GGC GTT GTC ATG ATC CTC ATG GTG CCC TCC       152
Leu Leu Phe Ala Ala Leu Gly Val Val Met Ile Leu Met Val Pro Ser
 20                  25                  30

CTC ATC AAG CAG CAG GTG CTC AAG AAT GTC CGC ATA GAC CCG AGC AGC       200
Leu Ile Lys Gln Gln Val Leu Lys Asn Val Arg Ile Asp Pro Ser Ser
 35                  40                  45                  50

CTG TCC TTC GGG ATG TGG AAG GAG ATC CCC GTC CCT TTC TAC TTG TCT       248
Leu Ser Phe Gly Met Trp Lys Glu Ile Pro Val Pro Phe Tyr Leu Ser
                 55                  60                  65

GTC TAC TTC TTC GAA GTG GTC AAC CCA AAC GAG GTC CTC AAC GGC CAG       296
Val Tyr Phe Phe Glu Val Val Asn Pro Asn Glu Val Leu Asn Gly Gln
             70                  75                  80

AAG CCA GTA GTC CGG GAG CGT GGA CCC TAT GTC TAC AGG GAG TTC AGA       344
Lys Pro Val Val Arg Glu Arg Gly Pro Tyr Val Tyr Arg Glu Phe Arg
                 85                  90                  95

CAA AAG GTC AAC ATC ACC TTC AAT GAC AAC GAC ACC GTG TCC TTC GTG       392
Gln Lys Val Asn Ile Thr Phe Asn Asp Asn Asp Thr Val Ser Phe Val
100                 105                 110

GAG AAC CGC AGC CTC CAT TTC CAG CCT GAC AAG TCG CAT GGC TCA GAG       440
Glu Asn Arg Ser Leu His Phe Gln Pro Asp Lys Ser His Gly Ser Glu
115                 120                 125                 130

AGT GAC TAC ATT GTA CTG CCT AAC ATC TTG GTC CTG GGG GGC TCG ATA       488
Ser Asp Tyr Ile Val Leu Pro Asn Ile Leu Val Leu Gly Gly Ser Ile
                135                 140                 145

TTG ATG GAG AGC AAG CCT GTG AGC CTG AAG CTG ATG ATG ACC TTG GCG       536
Leu Met Glu Ser Lys Pro Val Ser Leu Lys Leu Met Met Thr Leu Ala
            150                 155                 160

CTG GTC ACC ATG GGC CAG CGT GCT TTT ATG AAC CGC ACA GTT GGT GAG       584
Leu Val Thr Met Gly Gln Arg Ala Phe Met Asn Arg Thr Val Gly Glu
        165                 170                 175

ATC CTG TGG GGC TAT GAC GAT CCC TTC GTG CAT TTT CTC AAC ACG TAC       632
Ile Leu Trp Gly Tyr Asp Asp Pro Phe Val His Phe Leu Asn Thr Tyr
    180                 185                 190

CTC CCA GAC ATG CTT CCC ATA AAG GGC AAA TTT GGC CTG TTT GTT GGG       680
Leu Pro Asp Met Leu Pro Ile Lys Gly Lys Phe Gly Leu Phe Val Gly
195                 200                 205                 210

ATG AAC AAC TCG AAT TCT GGG GTC TTC ACT GTC TTC ACG GGC GTC CAG       728
Met Asn Asn Ser Asn Ser Gly Val Phe Thr Val Phe Thr Gly Val Gln
                215                 220                 225
```

| | | |
|---|---|---|
| AAT TTC AGC AGG ATC CAT CTG GTG GAC AAA TGG AAC GGA CTC AGC AAG<br>Asn Phe Ser Arg Ile His Leu Val Asp Lys Trp Asn Gly Leu Ser Lys<br>230 235 240 | 776 | |
| ATC GAT TAT TGG CAT TCA GAG CAG TGT AAC ATG ATC AAT GGG ACT TCC<br>Ile Asp Tyr Trp His Ser Glu Gln Cys Asn Met Ile Asn Gly Thr Ser<br>245 250 255 | 824 | |
| GGG CAG ATG TGG GCA CCC TTC ATG ACA CCC GAA TCC TCG CTG GAA TTC<br>Gly Gln Met Trp Ala Pro Phe Met Thr Pro Glu Ser Ser Leu Glu Phe<br>260 265 270 | 872 | |
| TTC AGC CCG GAG GCA TGC AGG TCC ATG AAG CTG ACC TAC AAC GAA TCA<br>Phe Ser Pro Glu Ala Cys Arg Ser Met Lys Leu Thr Tyr Asn Glu Ser<br>275 280 285 290 | 920 | |
| AGG GTG TTT GAA GGC ATT CCC ACG TAT CGC TTC ACG GCC CCC GAT ACT<br>Arg Val Phe Glu Gly Ile Pro Thr Tyr Arg Phe Thr Ala Pro Asp Thr<br>295 300 305 | 968 | |
| CTG TTT GCC AAC GGG TCC GTC TAC CCA CCC AAC GAA GGC TTC TGC CCA<br>Leu Phe Ala Asn Gly Ser Val Tyr Pro Pro Asn Glu Gly Phe Cys Pro<br>310 315 320 | 1016 | |
| TGC CGA GAG TCT GGC ATT CAG AAT GTC AGC ACC TGC AGG TTT GGT GCG<br>Cys Arg Glu Ser Gly Ile Gln Asn Val Ser Thr Cys Arg Phe Gly Ala<br>325 330 335 | 1064 | |
| CCT CTG TTT CTC TCC CAC CCC CAC TTT TAC AAC GCC GAC CCT GTG TTG<br>Pro Leu Phe Leu Ser His Pro His Phe Tyr Asn Ala Asp Pro Val Leu<br>340 345 350 | 1112 | |
| TCA GAA GCT GTT CTT GGT CTG AAC CCT AAC CCA AAG GAG CAT TCC TTG<br>Ser Glu Ala Val Leu Gly Leu Asn Pro Asn Pro Lys Glu His Ser Leu<br>355 360 365 370 | 1160 | |
| TTC CTA GAC ATC CAT CCG GTC ACT GGG ATC CCC ATG AAC TGT TCT GTG<br>Phe Leu Asp Ile His Pro Val Thr Gly Ile Pro Met Asn Cys Ser Val<br>375 380 385 | 1208 | |
| AAG ATG CAG CTG AGC CTC TAC ATC AAA TCT GTC AAG GGC ATC GGG CAA<br>Lys Met Gln Leu Ser Leu Tyr Ile Lys Ser Val Lys Gly Ile Gly Gln<br>390 395 400 | 1256 | |
| ACA GGG AAG ATC GAG CCA GTA GTT CTG CCG TTG CTG TGG TTC GAA CAG<br>Thr Gly Lys Ile Glu Pro Val Val Leu Pro Leu Leu Trp Phe Glu Gln<br>405 410 415 | 1304 | |
| AGC GGA GCA ATG GGT GGC AAG CCC CTG AGC ACG TTC TAC ACG CAG CTG<br>Ser Gly Ala Met Gly Gly Lys Pro Leu Ser Thr Phe Tyr Thr Gln Leu<br>420 425 430 | 1352 | |
| GTG CTG ATG CCC CAG GTT CTT CAC TAC GCG CAG TAT GTG CTG CTG GGG<br>Val Leu Met Pro Gln Val Leu His Tyr Ala Gln Tyr Val Leu Leu Gly<br>435 440 445 450 | 1400 | |
| CTT GGA GGC CTC CTG TTG CTG GTG CCC ATC ATC TGC CAA CTG CGC AGC<br>Leu Gly Gly Leu Leu Leu Val Pro Ile Ile Cys Gln Leu Arg Ser<br>455 460 465 | 1448 | |
| CAG GAG AAA TGC TTT TTG TTT TGG AGT GGT AGT AAA AAG GGC TCC CAG<br>Gln Glu Lys Cys Phe Leu Phe Trp Ser Gly Ser Lys Lys Gly Ser Gln<br>470 475 480 | 1496 | |
| GAT AAG GAG GCC ATT CAG GCC TAC TCT GAG TCC CTG ATG TCA CCA GCT<br>Asp Lys Glu Ala Ile Gln Ala Tyr Ser Glu Ser Leu Met Ser Pro Ala<br>485 490 495 | 1544 | |
| GCC AAG GGC ACG GTG CTG CAA GAA GCC AAG CTA TAGGGTCCTG AAGACACTAT<br>Ala Lys Gly Thr Val Leu Gln Glu Ala Lys Leu<br>500 505 | 1597 | |
| AAGCCCCCCA AACCTGATAG CTTGGTCAGA CCAGCCACCC AGTCCCTACA CCCCGCTTCT | 1657 | |
| TGAGGACTCT CTCAGCGGAC AGCCCACCAG TGCCATGGCC TGAGCCCCCA GATGTCACAC | 1717 | |
| CTGTCCGCAC GCACGGCACA TGGATGCCCA CGCATGTGCA AAAACAACTC AGGGACCAGG | 1777 | |
| GACAGACC | 1785 | |

(2) INFORMATION FOR SEQ ID NO:4:

(i) SEQUENCE CHARACTERISTICS:
        (A) LENGTH: 509 amino acids
        (B) TYPE: amino acid
        (D) TOPOLOGY: linear (ii) MOLECULE TYPE: protein (ix) FEATURE:
        (A) NAME/KEY: misc. feature
        (B) LOCATION: 1..509
        (D) OTHER INFORMATION: /Function = "Amino acid sequence for
            the murine Scavenger Receptor Class BI."

(xi) SEQUENCE DESCRIPTION: SEQ ID NO:4:

```
Met Gly Gly Ser Ser Arg Ala Arg Trp Val Ala Leu Gly Leu Gly Ala
 1               5                  10                  15

Leu Gly Leu Leu Phe Ala Ala Leu Gly Val Val Met Ile Leu Met Val
             20                  25                  30

Pro Ser Leu Ile Lys Gln Gln Val Leu Lys Asn Val Arg Ile Asp Pro
         35                  40                  45

Ser Ser Leu Ser Phe Gly Met Trp Lys Glu Ile Pro Val Pro Phe Tyr
     50                  55                  60

Leu Ser Val Tyr Phe Phe Glu Val Val Asn Pro Asn Glu Val Leu Asn
 65                  70                  75                  80

Gly Gln Lys Pro Val Val Arg Glu Arg Gly Pro Tyr Val Tyr Arg Glu
                 85                  90                  95

Phe Arg Gln Lys Val Asn Ile Thr Phe Asn Asp Asn Asp Thr Val Ser
            100                 105                 110

Phe Val Glu Asn Arg Ser Leu His Phe Gln Pro Asp Lys Ser His Gly
        115                 120                 125

Ser Glu Ser Asp Tyr Ile Val Leu Pro Asn Ile Leu Val Leu Gly Gly
    130                 135                 140

Ser Ile Leu Met Glu Ser Lys Pro Val Ser Leu Lys Leu Met Met Thr
145                 150                 155                 160

Leu Ala Leu Val Thr Met Gly Gln Arg Ala Phe Met Asn Arg Thr Val
                165                 170                 175

Gly Glu Ile Leu Trp Gly Tyr Asp Asp Pro Phe Val His Phe Leu Asn
            180                 185                 190

Thr Tyr Leu Pro Asp Met Leu Pro Ile Lys Gly Lys Phe Gly Leu Phe
        195                 200                 205

Val Gly Met Asn Asn Ser Asn Ser Gly Val Phe Thr Val Phe Thr Gly
    210                 215                 220

Val Gln Asn Phe Ser Arg Ile His Leu Val Asp Lys Trp Asn Gly Leu
225                 230                 235                 240

Ser Lys Ile Asp Tyr Trp His Ser Glu Gln Cys Asn Met Ile Asn Gly
                245                 250                 255

Thr Ser Gly Gln Met Trp Ala Pro Phe Met Thr Pro Glu Ser Ser Leu
            260                 265                 270

Glu Phe Phe Ser Pro Glu Ala Cys Arg Ser Met Lys Leu Thr Tyr Asn
        275                 280                 285

Glu Ser Arg Val Phe Glu Gly Ile Pro Thr Tyr Arg Phe Thr Ala Pro
    290                 295                 300

Asp Thr Leu Phe Ala Asn Gly Ser Val Tyr Pro Pro Asn Glu Gly Phe
305                 310                 315                 320

Cys Pro Cys Arg Glu Ser Gly Ile Gln Asn Val Ser Thr Cys Arg Phe
                325                 330                 335
```

-continued

```
Gly Ala Pro Leu Phe Leu Ser His Pro His Phe Tyr Asn Ala Asp Pro
            340             345             350

Val Leu Ser Glu Ala Val Leu Gly Leu Asn Pro Asn Pro Lys Glu His
            355             360             365

Ser Leu Phe Leu Asp Ile His Pro Val Thr Gly Ile Pro Met Asn Cys
    370             375             380

Ser Val Lys Met Gln Leu Ser Leu Tyr Ile Lys Ser Val Lys Gly Ile
385             390             395             400

Gly Gln Thr Gly Lys Ile Glu Pro Val Val Leu Pro Leu Leu Trp Phe
            405             410             415

Glu Gln Ser Gly Ala Met Gly Gly Lys Pro Leu Ser Thr Phe Tyr Thr
            420             425             430

Gln Leu Val Leu Met Pro Gln Val Leu His Tyr Ala Gln Tyr Val Leu
            435             440             445

Leu Gly Leu Gly Gly Leu Leu Leu Leu Val Pro Ile Ile Cys Gln Leu
    450             455             460

Arg Ser Gln Glu Lys Cys Phe Leu Phe Trp Ser Gly Ser Lys Lys Gly
465             470             475             480

Ser Gln Asp Lys Glu Ala Ile Gln Ala Tyr Ser Glu Ser Leu Met Ser
            485             490             495

Pro Ala Ala Lys Gly Thr Val Leu Gln Glu Ala Lys Leu
            500             505
```